US008041417B2

(12) United States Patent
Jonckheere et al.

(10) Patent No.: US 8,041,417 B2
(45) Date of Patent: Oct. 18, 2011

(54) METHOD AND SYSTEM FOR DYNAMICAL SYSTEMS MODELING OF ELECTROCARDIOGRAM DATA

(75) Inventors: Edmond Jonckheere, Los Almitos, CA (US); Fariba Ariaei, Middletown, PA (US); Timothy Callahan, Northridge, CA (US); William Stuppy, Los Angeles, CA (US)

(73) Assignees: University of Southern California, Los Angeles, CA (US); Biomedical Systems Corporation, Maryland Heights, MO (US)

( * ) Notice: Subject to any disclaimer, the term of this patent is extended or adjusted under 35 U.S.C. 154(b) by 474 days.

(21) Appl. No.: 12/359,846

(22) Filed: Jan. 26, 2009

(65) Prior Publication Data

US 2009/0326401 A1 Dec. 31, 2009

Related U.S. Application Data

(60) Provisional application No. 61/062,366, filed on Jan. 25, 2008.

(51) Int. Cl.
*A61B 5/04* (2006.01)

(52) U.S. Cl. ........................................................ 600/516

(58) Field of Classification Search .................. 600/516
See application file for complete search history.

(56) References Cited

U.S. PATENT DOCUMENTS

| 6,438,409 | B1 * | 8/2002 | Malik et al. .................. 600/512 |
| 6,993,377 | B2 | 1/2006 | Flick et al. |
| 7,038,595 | B2 | 5/2006 | Seely |
| 2005/0010123 | A1 | 1/2005 | Charuvastra et al. |

OTHER PUBLICATIONS

PCT International Search Report and Written Opinion, PCT Application No. PCT/US09/31997, Mar. 27, 2009, 9 pages.

* cited by examiner

*Primary Examiner* — George Manuel
(74) *Attorney, Agent, or Firm* — Senniger Powers LLP

(57) ABSTRACT

Electrocardiogram data is received in association with a subject, the electrocardiogram data comprising a series of RR intervals and a series of QT intervals. A first value which indicates an amount by which uncertainty associated with the QT intervals is reduced given the RR intervals is generated. A second value which indicates an amount by which uncertainty associated with the RR intervals is reduced given the QT intervals is generated. The subject is determined to be associated with a low risk of cardiac dysfunction responsive to the first value exceeding the second value and a result of the determination is provided.

25 Claims, 11 Drawing Sheets

METHOD AND SYSTEM FOR DYNAMICAL SYSTEMS MODELING OF ELECTROCARDIOGRAM DATA

This application claims the benefit of provisional application 61/062,366 filed Jan. 25, 2008, the entirety of which is incorporated by reference herein.

BACKGROUND OF THE INVENTION

1. Field of the Invention

This invention pertains to a system for diagnosing a risk of cardiac dysfunction based on electrocardiogram data. Specifically, this invention pertains to the use of dynamical systems modeling techniques to identify metrics used to diagnose heart health.

2. Background

An electrocardiogram (ECG) is a recording of the electrical activity of the heart over time. Cardiac cells are electrically polarized, that is, the insides of the cells are negatively charged with respect to their outside of the cells by means of pumps in the cell membrane that distribute ions (primarily potassium, sodium, chloride, and calcium) in order to keep the insides of these cells negatively charged (i.e. electronegative). Cardiac cells loose their internal electronegativity in depolarization. Depolarization is an electrical event which corresponds to heart contraction or "beating". In depolarization, loss of electronegativity is propagated from cell to cell, producing a wave of electrical activity that can be transmitted across the heart.

Electrical impulses in the heart originate in the sinoatrial node (SA Node) and travel through the heart muscle where they impart electrical initiation of "systole" or contraction of the heart. The electrical waves can be measured by electrodes (electrical contacts) placed on the skin of a subject. These electrodes measure the electrical activity of different parts of the heart muscle. An ECG displays the voltage between pairs of these electrodes, and the muscle activity that they measure, from different directions. This display indicates the rhythm of heart contraction.

FIG. 1 depicts the peaks in an electrocardiogram signal. Electrocardiogram signals are comprised of three major structures which are used to characterize the health of a subject's cardiac system, the "QRS complex", the "P wave" and the "T wave." The P wave is a structure in the ECG signal which corresponds to the depolarization of the atria as the main electrical vector is directed from the SA node to the Atrioventicular Node (AV node). The QRS complex is a structure in the ECG signal that corresponds to the depolarization of the ventricles. Because the ventricles contain more muscle mass than the atria, the QRS complex is larger than the P wave. The T wave is a structure in the ECG signal that corresponds to the "repolarization" or recovery of electronegativity in the ventricles after depolarization.

Heart rate variability (HRV) refers to the beat to beat alteration in heart rate. Heart rate variability can be determined based on electrocardiogram (ECG) signals. The "RR Interval" is the distance between consecutive R peaks in an electrocardiogram signal. The heart rate for a given time period is defined as the reciprocal of an RR interval (in seconds) multiplied by 60. Healthy hearts exhibit a large HRV, whereas an absence of variability or decreased variability is associated with cardiac or systemic dysfunction. The term "cardiac dysfunction", as used herein, refers to any type of abnormal functioning of the cardiac system including cardiac disease. Several studies have also shown that a reduction in heart rate variability is also predictive of a subject's likelihood of sudden death from cardiac dysfunction.

Another important interval used to diagnose heart health is the QT interval. The QT interval represents the total time needed for the ventricles to depolarize and regain electronegativity. The QT interval varies according to the heart rate and is typically corrected according to the heart rate. If the QT interval is abnormally lengthened or shortened, heart complications, including Torsade de Pointes (TDP) and sudden death can occur. Prolongation of the QT interval can be associated with certain metabolic and disease states, congenital disease states and adverse drug reaction.

Dynamical systems theory is an area of applied mathematics used to describe the behavior of complex dynamical systems, that is, systems whose states evolve with time in a manner which is difficult to predict over the long range. According to dynamical systems theory, systems may be characterized as being deterministic (meaning that their future states are, in theory, fully defined by their initial conditions, with no random elements involved) or non-deterministic (meaning the future states are random or undefined by their initial conditions). A periodic system is a system which deterministically returns to a same state over time. A random system is a system which is non-deterministic. Chaos theory is an area of dynamical systems theory which seeks to describe the behavior of certain dynamical systems that may exhibit dynamics that are highly sensitive to initial conditions. As a result of this sensitivity, the behavior of chaotic systems appears to be random. This behavior happens even though chaotic systems are deterministic, meaning that their future dynamics are difficult to predict even though their future dynamics are fully defined by their initial conditions, with no random elements involved. This behavior is known as deterministic chaos, or simply "chaos". This chaotic behavior is observed in natural systems, such as weather systems and is hypothesized to be observed in physiological systems including the cardiac system.

It has been proposed that physiological systems act as chaotic systems, even though this hypothesis is contrary to the classical paradigm of homeostasis. In homeostasis, physiological systems self-regulate through adjustments in order to maintain equilibrium and reduce variability. In contrast, this proposed hypothesis conjectures that a healthy physiological system exhibits characteristics of a chaotic system such as sensitivity to slight perturbations. This sensitivity and the associated responsiveness in the physiological system causes the system to produce a large variety of behaviors in the physiological system, such as the high variability/complexity in heart rate observed in subjects without cardiac disease or dysfunction. Conversely, the hypothesis proposes that unhealthy or dysfunctional biological systems are associated with a decreased sensitivity and have less variability in their behavior than the healthy systems. This corresponds to the low heart rate variability observed in subjects with poor heart health.

Early studies conducted by Dr. Chi-Sang Poon (Poon et al. (2001), Poon et al. (1997), Barhona and Poon (1996)) demonstrate that heart rate variability is not caused by random fluctuations but instead complex, deterministic patterns. Accordingly, a number of studies have applied different metrics traditionally used to study chaotic system to electrocardiogram data. Narayan et al. (1998) discovered that the times series RR interval data exhibit unstable periodic orbits (UPOs). A dense set of periodic orbits is indeed a criterion used to assert the deterministic chaotic dynamics of an underlying system. The Lyapunov Exponent is a metric used to characterize how chaotic a dynamic system is. Positive Lyapunov Exponents indicate that a system is chaotic. Unstable periodic orbits are chaotic and therefore are associated with positive Lyapunov Exponents. Similarly, Hashida and Takashi (1984) investigated the nature of the RR intervals during atrial fibrillation and determined that the distribution of the RR interval follows the Erlang distribution.

While these findings strengthen the hypothesis that the correspondence between heart rate variability and heart health is typical of a chaotic system, these studies have failed to provide a deeper understanding of the underlying dynamics of the cardiac system which cause the observed chaotic behavior. Accordingly, these estimates of chaotic behavior alone cannot reliably be used to predict heart health. Therefore, a deeper understanding of the role of chaos in cardiac dynamics is needed in order to develop accurate metrics of heart health and use these metrics in diagnostics.

BRIEF SUMMARY

The above and other needs are met by a computer-implemented method, a computer program product and a computer system for diagnosing a risk of cardiac disease based on a set of metrics that are derived from dynamical systems modeling of electrocardiogram data.

One aspect of the present invention provides a computer-implemented method for diagnosing cardiac dysfunction based on electrocardiogram data. Electrocardiogram data associated with a subject is received, the electrocardiogram data comprising a series of RR intervals and a series of QT intervals, wherein the series RR intervals corresponds, in part, to the series of QT intervals. A first value which indicates an amount by which uncertainty associated with the series of QT intervals is reduced given the series of RR intervals is generated. A second value which indicates an amount by which uncertainty associated with the series of RR intervals is reduced given the series of QT intervals is generated. The subject is determined to be associated with a low risk of cardiac dysfunction responsive to the first value exceeding the second value and a result of the determination is provided.

One aspect of the present invention provides a computer system for diagnosing cardiac dysfunction based on electrocardiogram data, the system comprising one or more computing devices and a memory. The system further comprises a reporting module stored in the memory and adapted to receive electrocardiogram data associated with a subject, the electrocardiogram data comprising a series of RR intervals and a series of QT intervals, wherein the series RR intervals corresponds, in part, to the series of QT intervals. The system further comprises a mutual information module stored in the memory and adapted to generate a first value which indicates an amount by which uncertainty associated with the series of QT intervals is reduced given the series of RR intervals and a second value which indicates an amount by which uncertainty associated with the series of RR intervals is reduced given the series of QT intervals. The system further comprises a diagnosis module stored in the memory and adapted to determine the subject to be associated with a low risk of cardiac dysfunction responsive to the first value exceeding the second value. The system further comprises a visualization module stored in the memory and adapted to provide a result of the determination.

Another aspect of the present invention provides a computer-readable storage medium encoded with computer program code for diagnosing cardiac dysfunction based on electrocardiogram data according to the above described method.

The features and advantages described in this summary and the following detailed description are not all-inclusive. Many additional features and advantages will be apparent to one of ordinary skill in the art in view of the drawings, specification, and claims hereof.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

As discussed above, a fundamental limitation of metrics used to assess chaotic behavior in dynamical systems, is that these metrics are simply "black box" metrics and do not provide insight into the underlying dynamics of the cardiac system. Therefore, these metrics cannot be accurately used to diagnose cardiac dysfunction. Accordingly, the focus of the present invention was to iteratively propose and validate hypotheses of the underlying mechanisms governing the dynamics of heart systems in order to develop metrics that can accurately be used to diagnose a risk of cardiac dysfunction. Based on these metrics, computational methods, computer program products and computer systems for diagnosing cardiac dysfunction based on electrocardiogram data associated with a subject are presented herein.

A hypothesis of heart dynamics based on Poincaré recurrence and strongly mixing theorems was proposed and validated in order to develop metrics used to diagnose cardiac dysfunction. In the proposed hypothesis, the RR interval corresponds to the compound Poincaré return time of the heart dynamical system.

Figure 1:
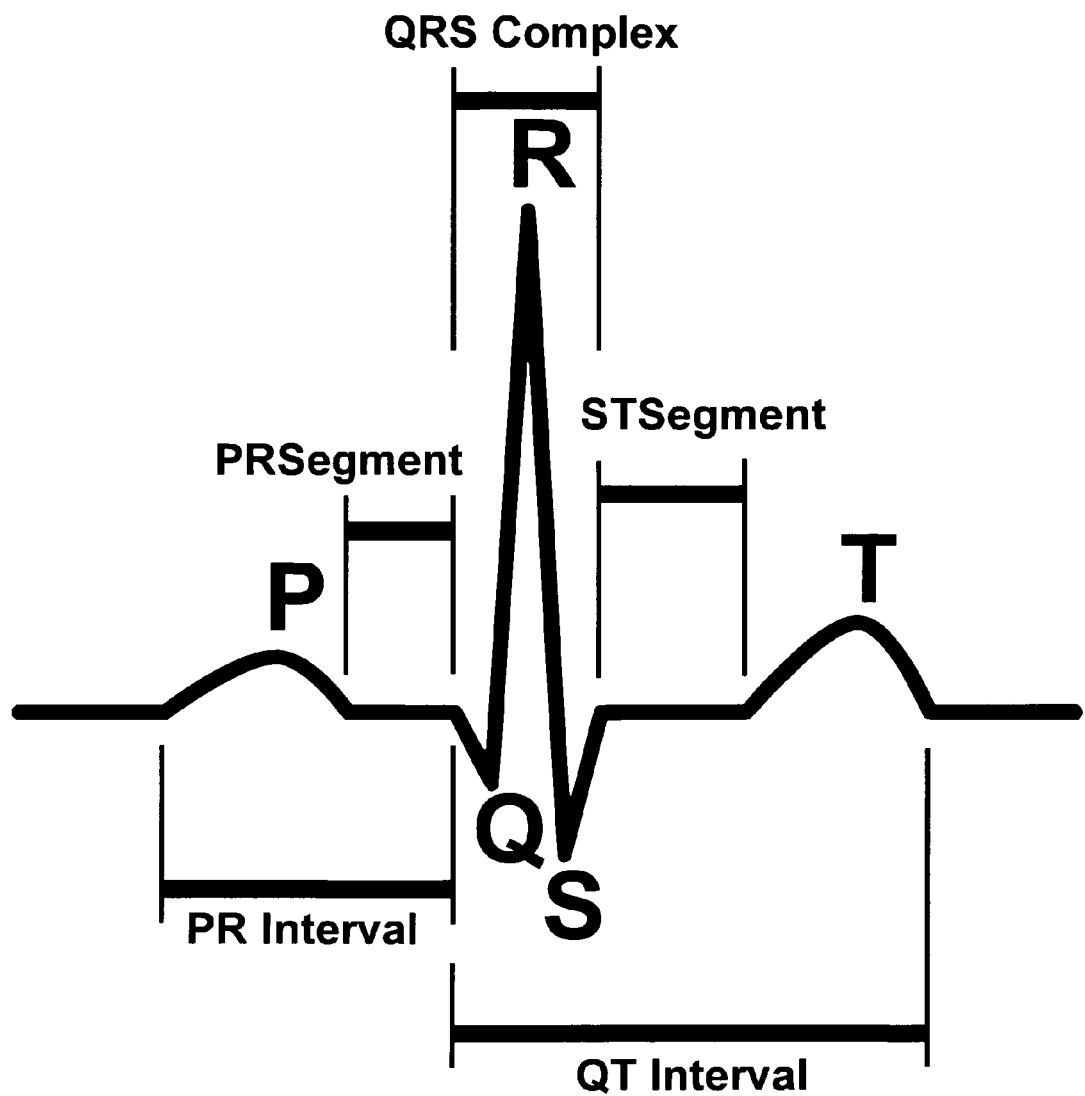
FIG. 1 illustrates an interval of an electrocardiogram and the characteristic structures within the interval.
Figure 2:
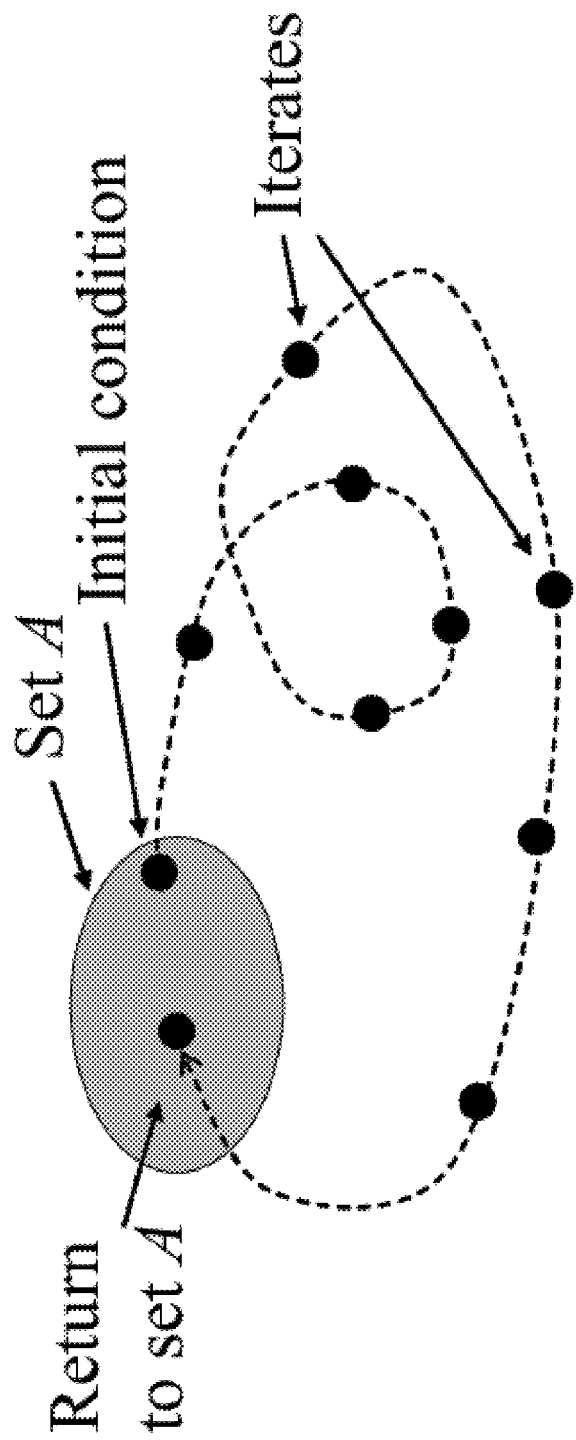
FIG. 2 illustrates the concept of Poincaré recurrence.

The Poincaré recurrence theorem states that certain abstract dynamical systems will, after a sufficiently long time, return to a state very close to the initial state (i.e. an attractor state). FIG. 2 illustrates the concept of Poincaré recurrence. The Poincaré recurrence time is the length of time elapsed until the recurrence. The Poincaré recurrence theorem states: For any $E \in \Sigma$, the set of those points x of E such that $f^n(x) \in E$ for all $n > 0$ has measure zero.

In other words, almost every point of E returns to E. In fact, almost every point returns indefinitely often; i.e. $\mu(\{x \in E:$ there exists N such that $f^n(x) \notin E$ for all $n > N\}) = 0$. The Poincaré recurrence time is based on Ergodic hypothesis which states that, over long periods of time, the time spent by a particle in some region of the phase space of microstates with the same energy is proportional to the volume of this region, i.e., that all accessible microstates are equally probable over a long period of time.

The hypothesis presented herein proposes that the system of cardiac depolarization and repolarization which causes the heart to beat is a strongly mixing dynamic system. This hypothesis further proposes that the RR interval corresponds to the compound Poincaré recurrence time of this system.

Scatter Plot Analysis

In order to validate the hypothesis that the RR interval corresponds to the Poincaré return time of the cardiac system, scatter plots of RR Interval Data were constructed based on ECG data obtained from 66 "normal" subjects (i.e. subjects without known cardiac dysfunction) and ECG data obtained from 12 subjects under several conditions in a clinical trial of a drug. These data are described in detail below in the section entitled "Clinical Data". The Poincaré return time hypothesis is also consistent with the Erlang fit.

Figure 3:
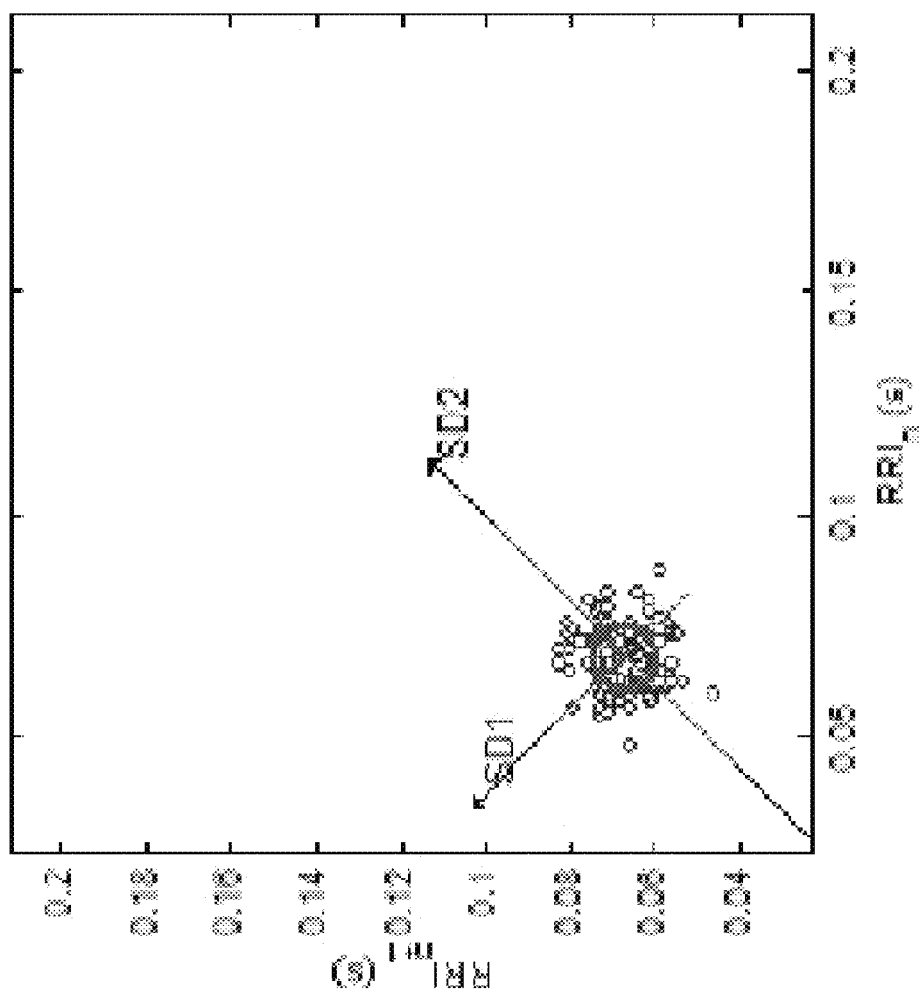
FIG. 3 illustrates a scatter plot of RR intervals according to non-linear dynamics.

The scatter plot, a technique taken from nonlinear dynamics, portrays the nature of RR interval fluctuations in the heart rate dynamics. Scatter plot analysis is a quantitative-visual technique whereby the shape of the plot is categorized into functional classes that indicate the degree of cardiac dysfunction in a subject. FIG. 3 illustrates a scatter plot of RR intervals from a subject without known cardiac dysfunction. This type of plot provides summary information as well as detailed beat-to-beat information on the behavior of the heart. The geometry of the scatter plot is essential and can be described by fitting an ellipse to the graph. The ellipse is fitted onto the so called line-of-identity at 45 degrees to the normal axis. The standard deviation of the points which were perpendicular to the line-of-identity denoted by SD1 describes short-term heart rate variability which is mainly caused by respiratory sinus arrhythmia (RSA). The standard deviation along the line-of-identity denoted by SD2 describes long term heart rate variability.

Figure 4:
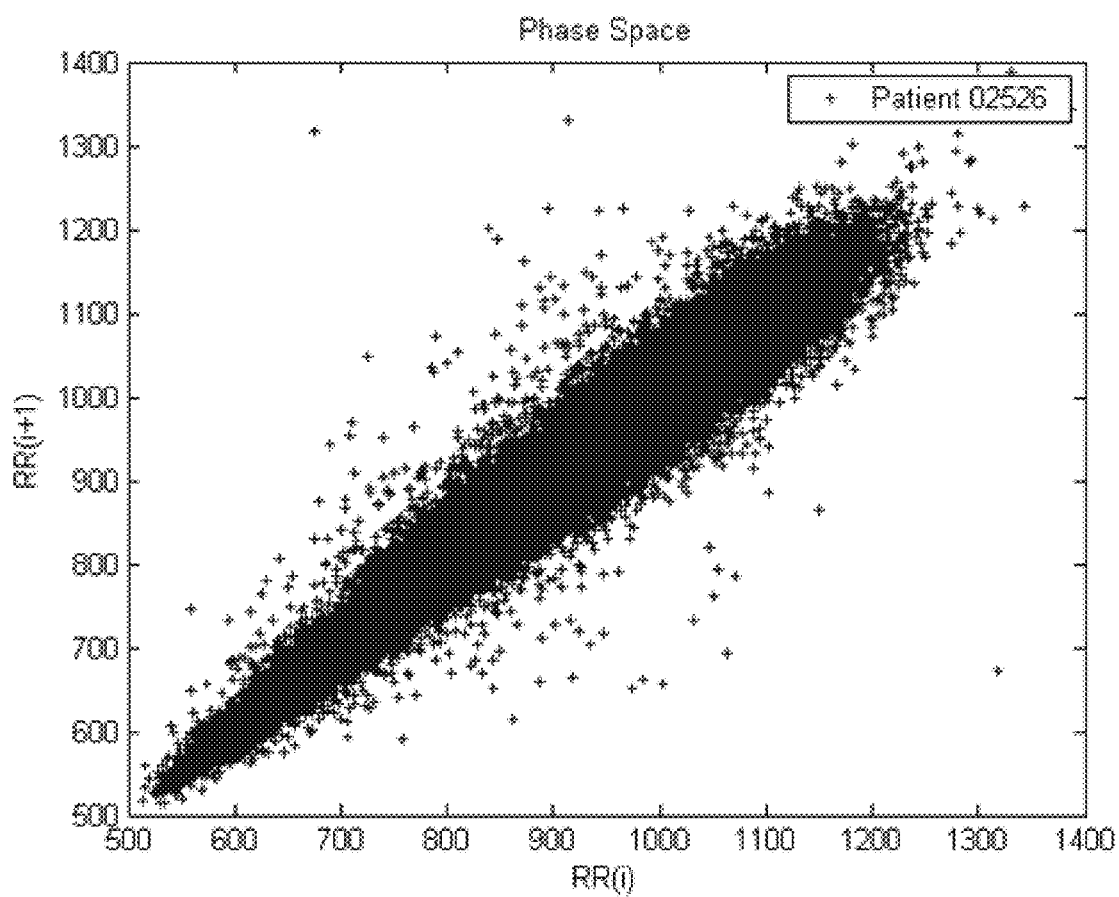
FIG. 4 illustrates a scatter plot of RR intervals from a subject without known cardiac dysfunction.

FIG. 4 illustrates a scatter plot of RR intervals according to nonlinear dynamics. This "RR interval scatter plot" considers the scatter plot as the two dimensional (2-D) reconstructed RR interval phase spaces. In other words, each RR interval RR(i) in the series of RR intervals is plotted against the subsequent RR interval RR(i+1). In dynamical system theory, the reconstructed RR interval phase spaces describe the dynamics of the cardiac system by projecting the reconstructed attractor. Attractor reconstruction refers to methods of using geometrical and topological information about a dynamical attractor from observations. These methods have been developed as a means to reconstruct the phase space of the system, specifically for experimental and naturally occurring chaotic dynamical systems, which the phase space and a mathematical description of the system are often unknown. Since the evolution of a dynamical system can be described by its phase space, it is very important to reconstruct the phase space of the system. Herein, we proceed from the hypothesis that the dynamics of the SA node which generates the RR intervals is a dynamical attractor.

The RR interval scatter plot typically appears as an elongated cloud of points oriented along the line-of-identity. The dispersion of points in the scatter plot perpendicular to the line-of-identity reflects the level of short term heart rate variability. The dispersion of points along the line-of-identity is thought to indicate the level of long-term heart rate variability. The scatter plots were analyzed quantitatively by calculating the standard deviations of the distances of the RR(i) to the lines y=x and y=−x+2$RR_m$, where $RR_m$ is the mean of all RR(i). The standard deviations are referred to as SD1 and SD2, respectively. SD1 related to the fast beat-to-beat variability in the data, while SD2 describes the longer-term variability of RR(i).

RR interval scatter plots of the type illustrated in FIG. 3 and FIG. 4 were generated for each subject using standard plotting functions available in the MATLAB™ numerical computing environment and programming language. The RR Interval Scatter plots for RR interval data associated with the normal subjects are included in pgs. 43-106 of provisional application 61/062,366. The RR Interval Scatter plots for RR interval data associated with Clinical Trial subjects are included in pgs. 110-180 of provisional application 61/062,366. The scatter plot of RR intervals (with lag one) for the subject data generally showed two morphologically distinct distributions: (I) an almost oval or "comet" shaped morphology and (II) non-oval shaped morphology. The scatter plots with the oval morphology were associated with subjects with a normal cardiac system (i.e. not associated with any known cardiac dysfunction). The scatter plots with the non-oval morphology were associated with subjects with abnormal or dysfunctional cardiac systems and cardiac systems of subjects administered with pharmaceutically active compounds. Overall, the "normal" subjects RR Interval scatter plots showed an oval morphology. The non-oval morphology was generally observed in the RR Interval Scatter Plots associated with the clinical trial patients. The results are consistent with the hypothesis that the RR interval is equal to the Poincare return time for subjects which are not known to have cardiac dysfunction.

Erlang Distribution Analysis

In conjunction with the scatter plot analysis, subject data was fit to Erlang distributions in order to validate the hypothesis that the RR interval corresponds to the compound Poincaré return time.

The Erlang distribution is a continuous probability distribution with wide applicability primarily due to its relation to the exponential and Gamma distributions. The Erlang distribution was developed by A. K. Erlang in order to examine the number of telephone calls which might be made at the same time to the operators of the switching stations. This work on telephone traffic engineering has been expanded to consider waiting times in queuing systems in general. The distribution is now used in the field of stochastic processes. The Erlang distribution also occurs as a description of the rate of transition of elements through a system of compartments. Such systems are widely used in biology and ecology. The Erlang distribution is the distribution of the sum of k independent identically distributed random variables each having an exponential distribution.

Histograms of RR interval data for the subjects were fit to the Erlang distribution using code developed in the MATLAB™ programming language and the SAS™ programming language. Parameters which described the best fit of the Erlang distribution to the RR Interval histograms using a "gamfit" function in MATLAB™ which provided maximum likelihood estimates (MLEs) for the parameters of a gamma distribution given the histogram data. The Erlang distribution is a special case of the gamma distribution in which the parameter K is an integer. For each RR interval histogram, an Erlang distribution was generated and the chi-squared error between the generated Erlang distribution and the RR interval histogram was generated to measure how well the RR interval histograms fit to the Erlang distribution. The least square error values calculated for the normal subjects are included in Appendix A. The least square error values calculated for the clinical trial subjects are included in Appendix C.

Figure 5:
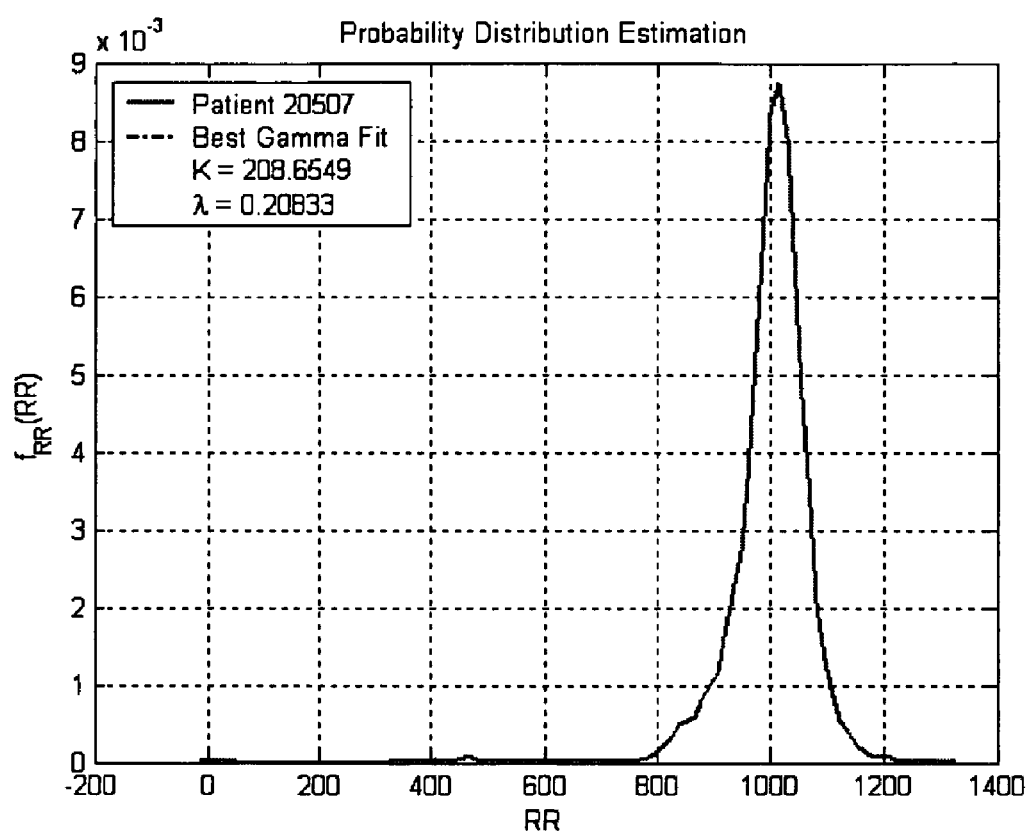
FIG. 5 illustrates a graph of the RR histogram data used to evaluate a fit to the Erlang distribution.

FIG. 5 illustrates a graph of the RR histogram data used to evaluate a fit to the Erlang distribution. Graphs of the RR interval histogram data and the associated Erlang distributions for the normal subjects are included in pgs. 399-463 of provisional patent application 61/062,366. Data for some, but not all of the "normal" subjects was observed to have an Erlang distribution based on the value of the least square error being below a threshold value. For these patients the least square error showed an unexpectedly good fit of which values less than 1e-05. Graphs of the RR interval histogram data and fitting parameters for the clinical trial subjects are included in pgs. 495-565 of provisional patent application 61/062,366.

It was further observed that there was weak correlation in the series of RR intervals associated with each of the subjects. This weak correlation within the series or sequence corresponds to work performed by N. Haydn (2004) which demonstrates that for a large class of mixing dynamical systems, the return event is a Poisson process.

The difference between the observed Erlang distribution in the RR Interval data and the hypothesis that the return event is a Poisson process is resolved by the hypothesis that the RR interval contains k>1 return times. The probability density function of the Erlang distribution is:

$$f(x; k, \lambda) = \frac{\lambda^k x^{k-1} e^{-\lambda x}}{(k-1)!} \text{ for } x > 0.$$

Given a Poisson distribution with a rate of change $\lambda$, the distribution function indicates the waiting times until the $k^{th}$ Poisson event. This distribution represents the sum of a series of exponential distributions. The parameter k is called the shape parameter and the parameter $\lambda$ is called the rate parameter.

These results supported a second complementary hypothesis regarding the dynamics of the SA node. The SA node regulates the RR intervals by initiating depolarization. Proceeding from the initial hypothesis, it was hypothesized that the SA node acts as "dynamical attractor" in the cardiac system and a heartbeat is emitted when the state of the SA attractor enters some finite region A, so that the interval would have been the Poincare return time to A. Unfortunately, the theoretically exponential distribution of the Poincare return time did not fit the histograms generated from subject RR interval data. However, the theoretical Erlang distribution of the k-fold return time provided a coefficients which indicated a good fit to histograms generated from RR interval data, for some but not all of the normal subjects. Therefore, the coefficient which indicates the fit of the RR interval data to the Erlang distribution provides a stringent metric for assessing cardiac health.

Physiologically, the multiple return times may correspond to non-linear synchronization of the cells responsible for the depolarization which causes the heart to beat. We hypothesize that each R peaks or "beats" is emitted after k returns of a state w of the underlying abstract system to a state A. It is well known that the synchronization of the many cells responsible for depolarization at a rate consistent with the heart beat creates signals at frequency which is an integer multiple of the higher frequency (Michaels et al., 1987).

These results were further interpreted in view of the previous contradictory observation by Hashida and Takashi that the Erlang Distribution was observed for RR Interval data from subjects with atrial fibrillation (a type of cardiac dysfunction). It was noted that in the Hashida and Takashi study, the subjects were administered digitalis, a medication used to treat cardiac dysfunction. Specifically, digitalis is used to increase cardiac contractility and as an antiarrhythmic agent in atrial fibrillation. Therefore, the two seemingly contradictory observations may be resolved if it is assumed that the treatment using digitalis in the Hashieda and Takashi study restored cardiac contractility in the subjects producing a heart rate variability in the subjects which were similar to the heart rate variability observed in normal subjects in the present study.

Chaos Metrics

Based on the validation of this hypothesis, additional metrics used to assess chaos in dynamic systems were calculated based on subject data and correlated to data generated from the Erlang distribution and scatter plot analyses in order to gain further insight into the heart dynamics. The statistical properties of heart dynamics were further assessed using correlation functions and their long term behavior.

Figure 6:
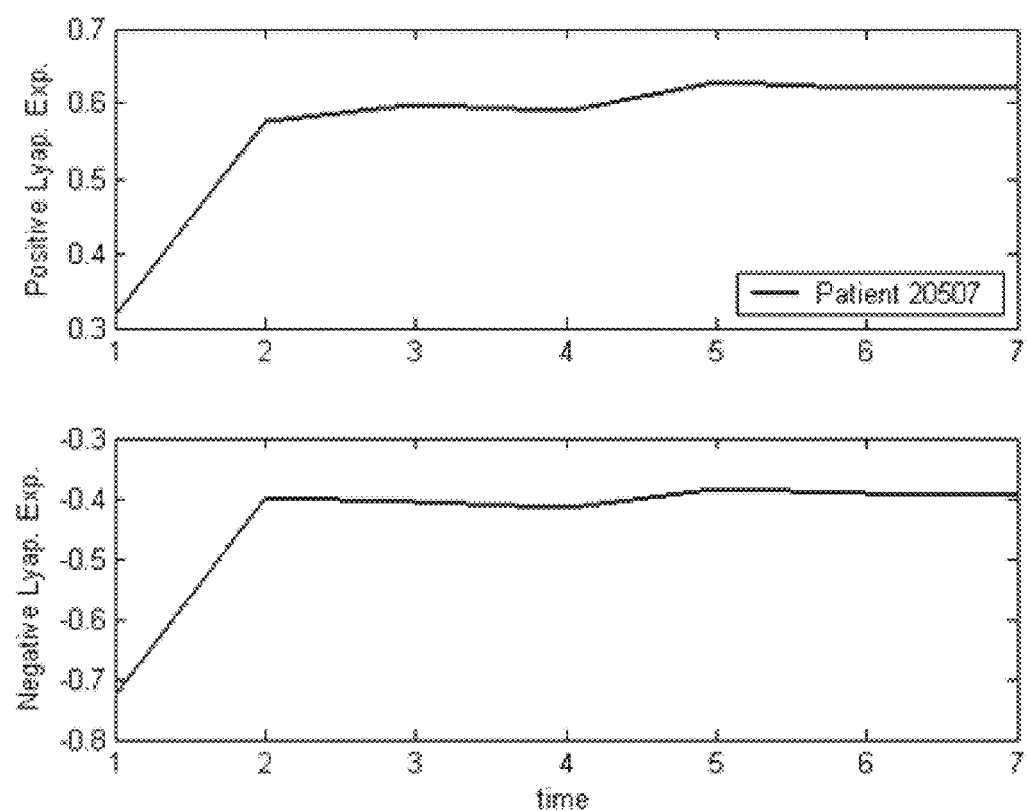
FIG. 6 illustrates a time-series plot of Lyapunov exponents.

Lyapunov exponents were calculated based on subject RR intervals as a metric of chaotic behavior in dynamical systems using program code developed in MATLAB™ and code developed in the C programming language. FIG. 6 illustrates a plot of Lyapunov exponents over time. Plots for each of the subjects are included on pgs. 399-565 of provisional application 61/062,366. The observation of positive Lyapunov exponents among all subjects confirmed that the dynamics of the heart rate demonstrates characteristics of a chaotic system. The Lyapunov exponents were calculated for embedding dimension equal to 2. Kolmogorov-Sinai entropy, or KS entropy, was also calculated based on the subject RR intervals. The KS entropy is equal to 0 for non-chaotic systems and greater than zero for chaotic systems. The Lyapunov exponent and KS entropy values associated with the normal subjects are included in Appendix A.

Lyapunov exponents were also calculated for the sequences of RR intervals derived from clinical data representing a set of five electrocardiogram recordings from a group of 12 subjects treated with drugs. The Lyapunov exponent and KS entropy values associated with the clinical trial subjects are included in Appendix C. This data is described in detail below in the section entitled "Clinical Data." Only one positive Lyapunov exponent observed for each of the five recording for each subject which was equivalent to the KS entropy for each subject. It was observed that the subjects that did not have Lyapunov exponents indicating chaotic behavior did not have a good fit to the Erlang distribution for the RR intervals. These results agree with the observation that the Erlang distributions are observed only in healthy cardiac systems which exhibit characteristics of chaotic systems.

The Lyapunov or Kaplan-Yorke dimension is a measure of the complexity of the system which is based on the Lyapunov exponents generated for the system. Lyapunov dimensions are described in detail below in the section entitled "Lyapunov Dimensions". Lyapunov dimensions typically range from D to D+1, where D represents the number of the Lyapunov exponents whose summation provides a positive value. Lower values of the Lyapunov dimension indicate less complexity and high values of the Lyapunov exponent indicate more complexity.

Canonical Correlation Analysis

Linear Canonical Correlation Analysis, Non Linear Canonical Correlation Analysis, Linear/Nonlinear Canonical Correlation Analysis of the Aggregated Data were performed on the electrocardiogram data from the normal and clinical trial subjects. These results are described in detail in the respectively titled sections below.

Mutual Information Analysis was performed on the series RR intervals and the corresponding series of QT intervals for each of the 66 normal subjects and the 12 subjects in the clinical trail under 5 different conditions. Mutual information metrics indicate how much the uncertainty in one variable is reduced by knowing another variable. In these analyses, the Kolmogorov-Sinai mutual information was used to generate values indicating how much the uncertainty in future QT interval data in the series of QT intervals is reduced by knowing the past RR interval data (MI(RR->QT)) and how much the uncertainty in future RR interval data in the series of RR intervals is reduced by knowing the past QT interval data (MI(QT->RR)). The mutual Kolmogorov-Sinai information is defined as $I(u-, y+)=KS(y+)-KS(y+|u-)$, where $KS(y+|u-)$ is the conditional entropy. The "lag" is an embedding dimension parameter used to generate the mutual information metrics. Although the value of the lag is arbitrary, best results are achieved when a lag is selected such that the data is separated as much as possible. Accordingly, mutual information values were generated using lag values of 25, 50, 100 and 500. Results from the normal subjects are tabulated in Appendix B. Results from the clinical trial subjects are tabulated in Appendix C. It was determined that the lag of 500 produced maximal separation in the RR and QT interval data.

Based on the generated values, it was observed that in the normal subjects the mutual information metric MI(RR->QT) generally exceeds the metric MI(QT->RR) and in clinical trial subjects at baseline the mutual information metric MI(QT->RR) generally exceeds the metric MI(RR->QT). Based on these results and hypotheses, the comparison of the two mutual information values MI(RR->QT) and MI(QT->RR) provide valuable metrics used to diagnose cardiac dysfunction.

Figure 11:
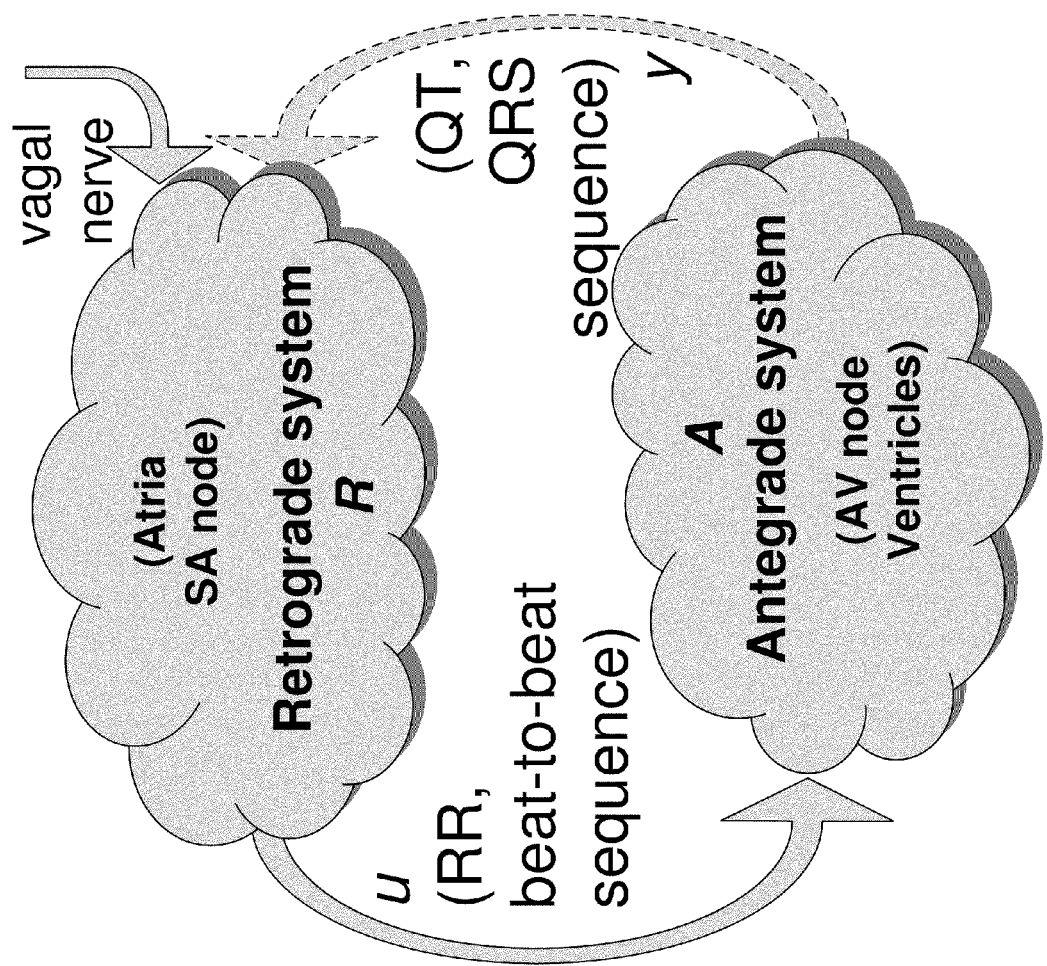
FIG. 11 is a conceptual illustration of a feedback loop hypothesis.

The observed results correspond to another complementary hypothesis that the RR and QT intervals are metrics of a feedback loop between the SA node and the AV node. This feedback loop is illustrated in FIG. 11. In healthy systems, the depolarization starting at the SA node controls this feedback and in cardiac dysfunction, the SA node looses its control and the AV node controls the system. These complimentary hypotheses further demonstrate that information theory metrics and dynamical modeling metrics may be used in conjunction to model functional cardiac systems and develop metrics that can predict a risk of cardiac dysfunction.

Based on the correlation between the observed results and the feedback loop hypothesis, another complimentary hypothesis regarding the role of the autonomic nervous system (ANS) and other factors extrinsic to the cardiac system in regulation of the RR-QT feedback loop may be proffered. It is well known that cardiac dysfunction can occur due to two distinct causes: intrinsic dysfunction and extrinsic dysfunction. In general, intrinsic cardiac dysfunction includes dysfunction due to an inherent, purely dynamical, aspect of the cardiac system which is internal to the cardiac system whereas extrinsic cardiac dysfunction includes dysfunction due to other factors external to the cardiac system which are not part of the cardiac system but cause a change in the function of the cardiac system such as pharmaceuticals and effect of the Autonomic Nervous System (ANS). Intrinsic cardiac dysfunction and extrinsic cardiac dysfunction by definition are mutually exclusive.

Proceeding from the above discussed hypothesis that the SA node acts as an "attractor" in healthy cardiac systems and the AV node acts as an attractor in unhealthy cardiac systems, it is hypothesized that the disruption to the feedback loop between the SA node and the AV node which causes cardiac dysfunction differs between intrinsic causation of cardiac dysfunction and extrinsic causation of cardiac dysfunction. It is further proposed that the causation of the dysfunction may be distinguished by further characterizing relationships within RR intervals and between the RR intervals and the QT intervals, which respectively can be used to characterize attractor behaviors of the SA node and the AV node.

Specifically, it is proposed that the degree of stationarity observed within the RR intervals data can be used to distinguish whether cardiac dysfunction is due to extrinsic or intrinsic factors. It is proposed that a higher degree of stationarity can be observed in extrinsic cardiac dysfunction due to the depleted effect of the Autonomic Nervous System (ANS) on the cardiac function via the vagus nerve and the SA node. For example, clinical trials have revealed such an increase of stationarity, as revealed by the Poincare meta-recurrence plots, concurrent with an increased dosage of some drug (see pgs. 560-566 of provisional patent application 61/062,366). As such a higher degree of stationarity would be an extrinsic cardiac dysfunction.

Information theory metrics such as mutual information metric may be further used to characterize the RR and QT interval data, thus providing distinction between intrinsic and extrinsic cardiac dysfunction. Since the entropy $KS(QT^+|RR^-)$ is conditioned upon the past RR interval data, the effect of the ANS via the SA node is removed, thus providing a window on the intrinsic heart function. Conversely, the second entropy $KS(RR^+|QT^-)$ is conditioned on the past QT interval data, dynamics based on factors intrinsic to the cardiac system are removed allowing for the assessment of extrinsic effects. Additionally, a higher degree of chaotic behavior within the RR interval data as indicated by Lyapunov coefficients or other chaos metrics such as entropy may indicate a higher likelihood of normal intrinsic cardiac function. The presence of deterministic chaos within RR interval data, as defined in dynamical system theory, is consistent with the hypothesis that the intrinsically heart function corresponds to a electro-hydro-dynamical attractor.

The distinction between intrinsic and extrinsic causation of cardiac dysfunction can be used to determine the relative effect of pharmaceuticals and the ANS system in subjects based on electrocardiogram data. Further, the ability to quantitatively determine the relative causation of extrinsic factors allows for the evaluation of pharmaceuticals and the ANS system in subjects with known cardiac dysfunction due to intrinsic (e.g. congenital) disorders such as congenital long QT syndrome.

Heart Health Prediction Server

Figure 7:
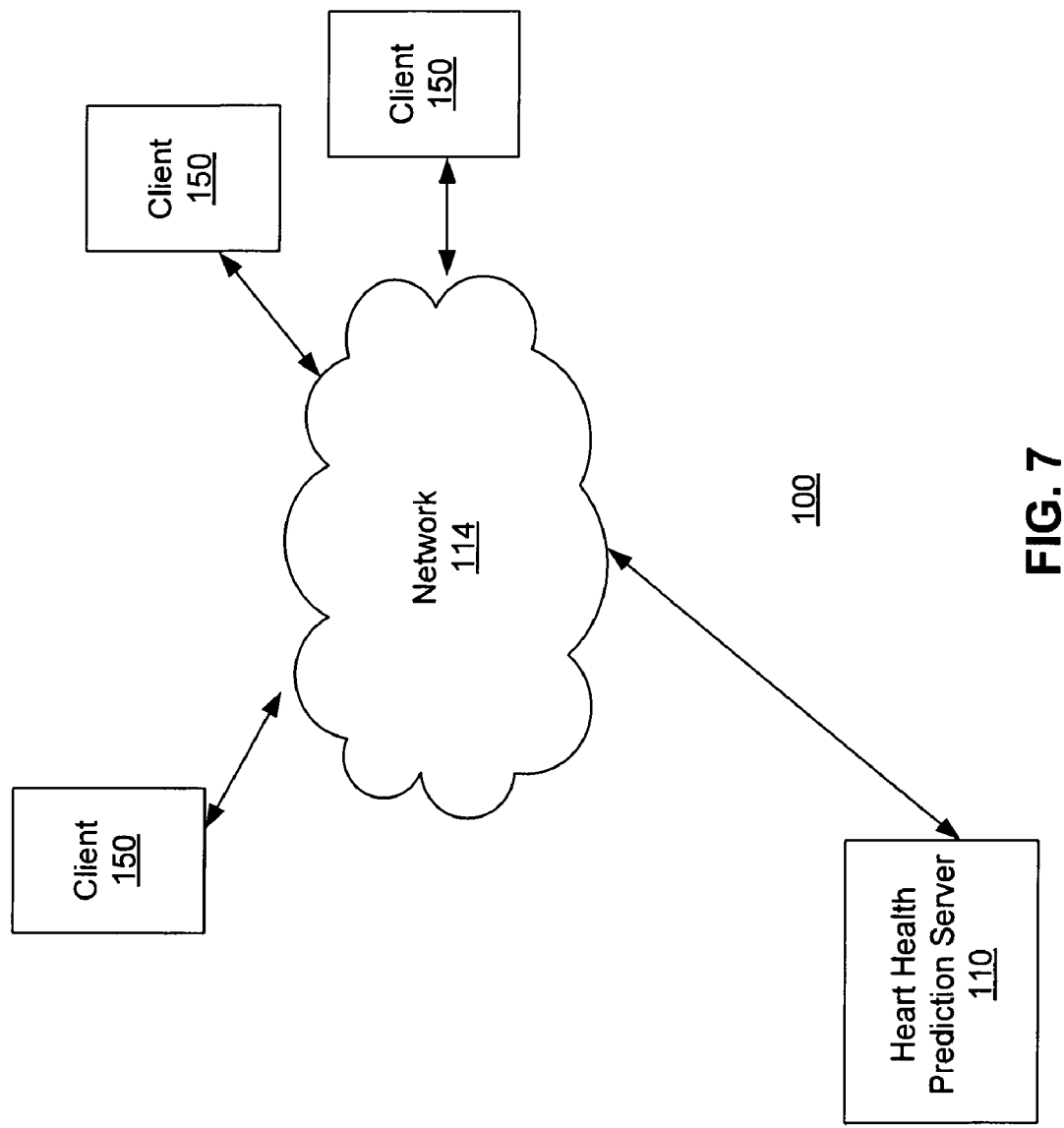
FIG. 7 is a high-level block diagram of a computing environment 100 according to one embodiment.

Based on the observed associations between the above described metrics and cardiac dysfunction, a heart health prediction sever 110 is presented herein. FIG. 7 is a high-level block diagram of a computing environment 100 according to one embodiment. FIG. 7 illustrates a heart health prediction sever 110 and three clients 150 connected by a network 114. The clients 150 transmit electrocardiogram data associated with a subject to the heart health prediction server 110. The heart health prediction server 110 received the electrocardiogram data from the clients 150 and generates metrics used to assess the risk of cardiac dysfunction according to the dynamical modeling techniques described above. In alternate embodiments, the heart health prediction server 110 receives the electrocardiogram data directly. The heart health prediction server 110 uses the metrics of heart health to determine a risk of cardiac dysfunction associated with the subject and transmit an indication of the risk to the clients 150. In some embodiments, the heart health prediction server 110 displays the indication of the risk directly to the clients 150. Only three clients 150 are shown in FIG. 7 in order to simplify and clarify the description. Embodiments of the computing environment 100 can have thousands or millions of clients 150 connected to the network 114.

The network 114 represents the communication pathways between the heart health prediction sever 110 and clients 150. In one embodiment, the network 114 is the Internet. The network 114 can also utilize dedicated or private communications links that are not necessarily part of the Internet. In one embodiment, the network 114 uses standard communications technologies and/or protocols. Thus, the network 114 can include links using technologies such as Ethernet, 802.11, integrated services digital network (ISDN), digital subscriber line (DSL), asynchronous transfer mode (ATM), etc. Similarly, the networking protocols used on the network 114 can include the transmission control protocol/Internet protocol (TCP/IP), the hypertext transport protocol (HTTP), the simple mail transfer protocol (SMTP), the file transfer protocol (FTP), etc. The data exchanged over the network 114 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

Figure 8:
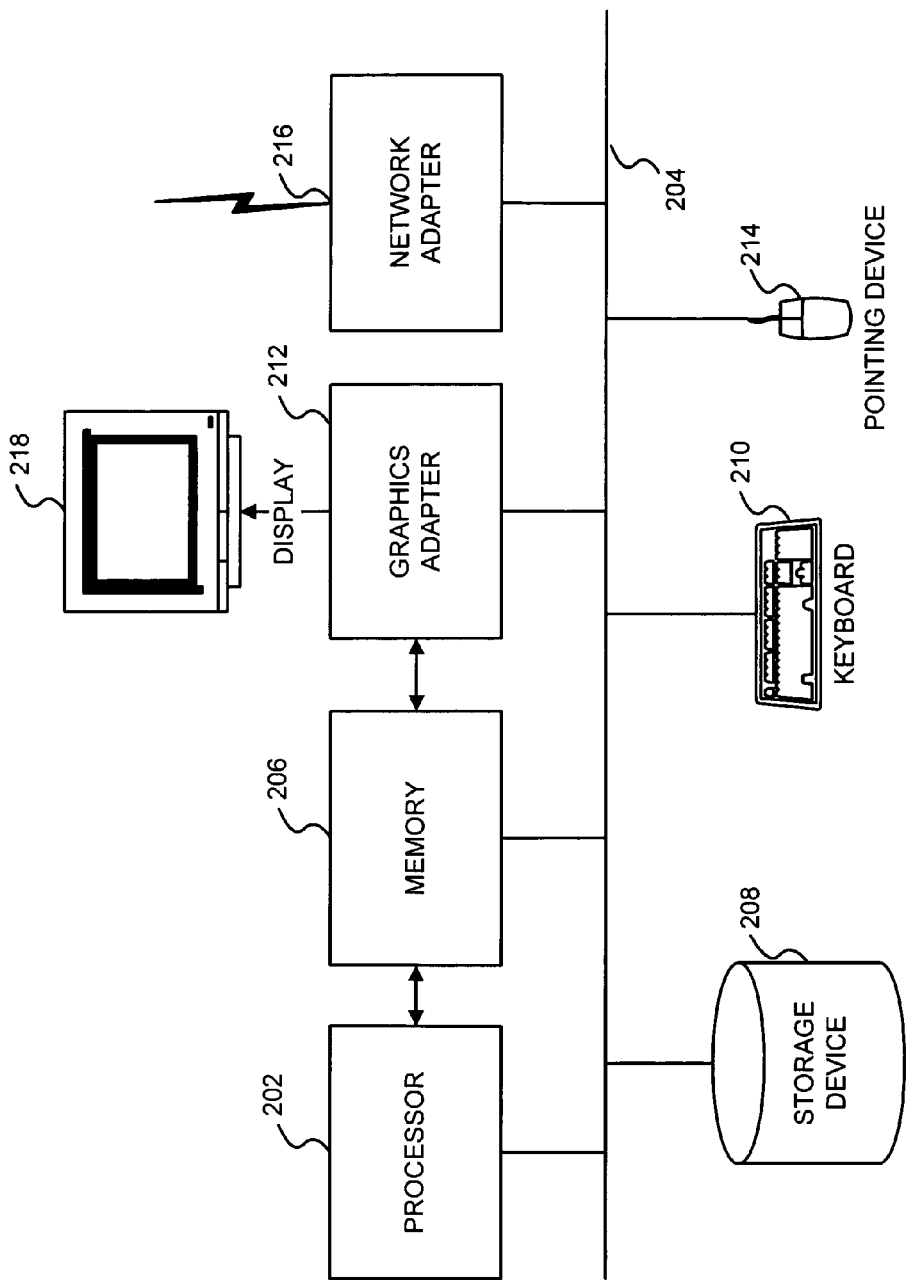
FIG. 8 is a high-level block diagram illustrating a typical computer for use as a heart health prediction server or client.

FIG. 8 is a high-level block diagram illustrating a typical computer 200 for use as a heart health prediction server 110 or client 150. Illustrated are a processor 202 coupled to a bus 204. Also coupled to the bus 204 are a memory 206, a storage device 208, a keyboard 210, a graphics adapter 212, a pointing device 214, and a network adapter 216. A display 218 is coupled to the graphics adapter 212.

The processor 202 may be any general-purpose processor such as an INTEL x86 compatible-CPU. The storage device 208 is, in one embodiment, a hard disk drive but can also be any other device capable of storing data, such as a writeable compact disk (CD) or DVD, or a solid-state memory device. The memory 206 may be, for example, firmware, read-only memory (ROM), non-volatile random access memory (NVRAM), and/or RAM, and holds instructions and data used by the processor 202. The pointing device 214 may be a mouse, track ball, or other type of pointing device, and is used in combination with the keyboard 210 to input data into the computer 200. The graphics adapter 212 displays images and other information on the display 218. The network adapter 216 couples the computer 200 to the network 114.

As is known in the art, the computer 200 is adapted to execute computer program modules. As used herein, the term "module" refers to computer program logic and/or data for providing the specified functionality. A module can be implemented in hardware, firmware, and/or software. In one embodiment, the modules are stored on the storage device 208, loaded into the memory 206, and executed by the processor 202.

The types of computers 200 utilized by the entities of FIG. 7 can vary depending upon the embodiment and the processing power utilized by the entity. For example, a client 150 that is a mobile telephone typically has limited processing power, a small display 218, and might lack a pointing device 214. The heart health prediction server 110, in contrast, may comprise multiple blade servers working together to provide the functionality described herein.

Figure 9:
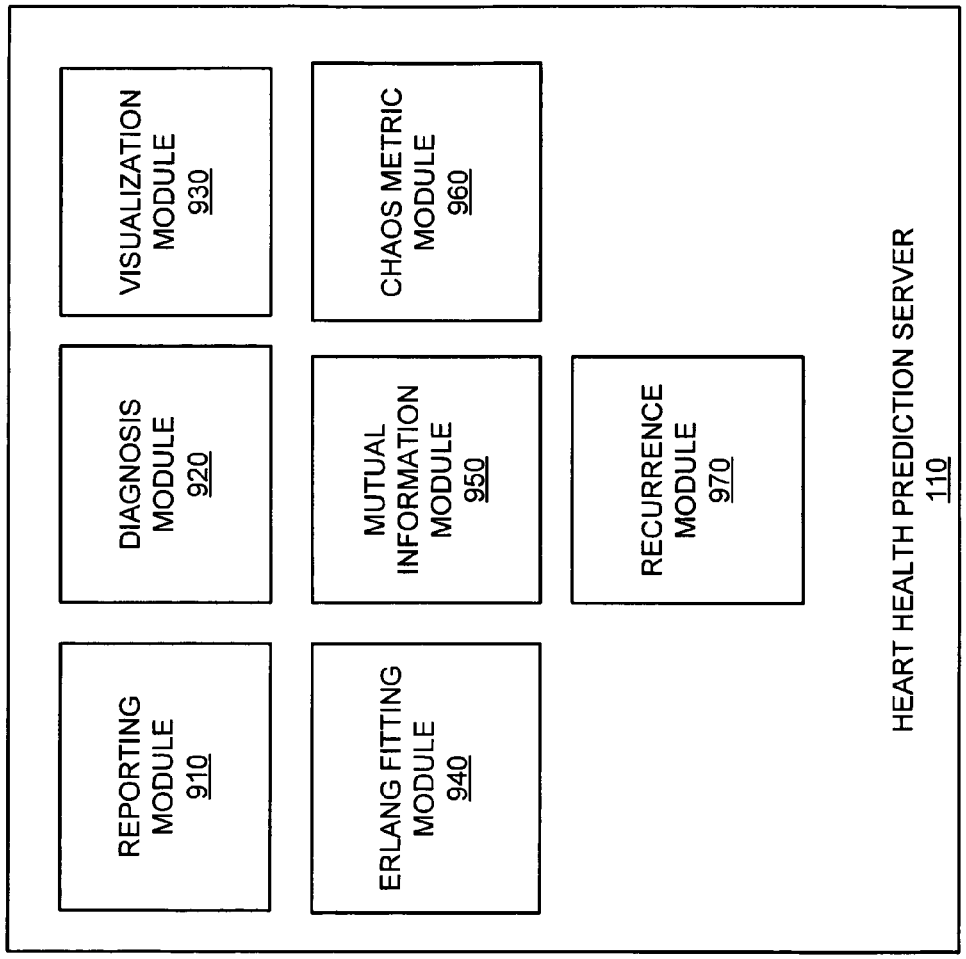
FIG. 9 is a high-level block diagram illustrating the heart health prediction server according to one embodiment.

FIG. 9 is a high-level block diagram illustrating the heart health prediction server 110 according to one embodiment. As shown in FIG. 9, the heart health prediction server 110 includes multiple modules. Those of skill in the art will recognize that other embodiments of the heart health prediction server 110 can have different and/or other modules than the ones described here, and that the functionalities can be distributed among the modules in a different manner.

The reporting module 910 functions to receive electrocardiogram data associated with subjects from the clients 150 comprising a series of QT intervals and a series of RR intervals. According to the embodiment, the reporting module 910 may correct the series of QT intervals using correction formulae such as Fridericia's and Bazett's correction formulae. The reporting module 910 is adapted to transmit the electrocardiogram data to the diagnosis module 920 for diagnosis. The reporting module 910 is further adapted to receive a value indicating the risk of cardiac dysfunction from the diagnosis module and transmit an indication of this value to the client 150. In some embodiments, the reporting module 910 is adapted to display an indication of the value indicating risk of other data used to generate the value indicating risk of cardiac dysfunction such as mutual information values, Erlang distribution values.

The diagnosis module 920 functions to generate values which indicate a risk of cardiac dysfunction based on the electrocardiogram data. The diagnosis module 920 communicates with the chaos metric module 960, the recurrence model 970, the Erlang fitting module 940 and the mutual information module 950 to receive metrics which indicate a subject's risk of cardiac dysfunction based on the electrocardiogram data. The diagnosis module 100 combines these metrics to determine the subject's risk of cardiac dysfunction.

The diagnosis module 920 may combine the metrics to generate a continuous value or a binary value. In one embodiment, the diagnosis module 920 generates a binary value indicating either a high risk of cardiac dysfunction or a low risk of cardiac dysfunction. In a specific embodiment, the diagnosis module 920 generates the binary value based on a first mutual information value which indicates an amount by which the uncertainty in future QT intervals of the series of QT intervals is reduced given the past RR interval data and a second mutual information value which indicates an amount by which the uncertainty in future RR intervals in the series of RR intervals is reduced given the past QT interval data. In this embodiment, the diagnosis module determines whether the first mutual information value is greater than the second mutual information value. If the diagnosis module 920 determines that the first mutual information value is greater than the second mutual information value, the diagnosis module 920 generates a value indicating a low risk of cardiac dysfunction. If the diagnosis module 920 determines that the second mutual information value is greater than the first mutual information value, the diagnosis module 920 generates a value indicating a high risk of cardiac dysfunction.

In some embodiments, the binary value may also be based on additional metrics and the mutual information metrics. In one embodiment, the diagnosis module 920 only generates a value indicating a high risk of cardiac dysfunction if a coefficient that indicates a least square fit of a histogram of the subject's RR interval data to an Erlang distribution is above a defined threshold value. Likewise, the diagnosis module 920 only generates a value indicating a low risk of cardiac dysfunction if a coefficient that indicates a fit of a histogram of the subject's RR interval data to an Erlang distribution is below a defined threshold value. In another embodiment, the diagnosis module 920 only generates a value indicating that a subject is associated with high risk of the cardiac dysfunction if one or more chaos metrics derived from the subject's electrocardiogram data are beneath a threshold value indicating a low quantity of chaos in the data. In this embodiment the diagnosis module 920 only generates a value indicating that a subject is associated with low risk of the cardiac dysfunction if one or more chaos metrics derived from the subject's electrocardiogram data are above a threshold value and indicate a high quantity of chaos in the data.

In some embodiments, the diagnosis module 920 further functions to generate values for subjects associated with a high risk cardiac dysfunction indicating whether the risk of cardiac dysfunction is due to intrinsic cardiac dysfunction or extrinsic cardiac dysfunction. In these embodiments, the diagnosis module 920 provides a determination of intrinsic and extrinsic cardiac dysfunction based additional metrics and/or additional threshold values. In some embodiments, the additional metrics may include stationarity metrics generated by the recurrence metric module 970 such as Poincare meta-recurrence metric or Dickey-Fuller Root of Unity metrics. In some embodiments, additional threshold values may be applied to conditional entropy metrics generated by the mutual information module 950 such as $KS(RR^+|QT^-)$ and $KS(QT^+|RR^-)$ in order to, respectively, quantify intrinsic and extrinsic effects in order to provide a determination whether the risk of cardiac dysfunction is due to intrinsic cardiac dysfunction or extrinsic cardiac dysfunction. According to the embodiment, other additional metric and/or threshold values may include, for example, Erlang fit. Since the Erlang fit can be justified on the ground of compounded Poincare return time, it is a purely dynamical feature, hence relevant to intrinsic cardiac function.

The chaos metric module 960 functions to generate values which quantify chaotic behavior in the subject's cardiac system based on the electrocardiogram data associated with a subject. The chaos metric module 960 generates chaos metrics including: Lyapunov coefficients, Lyapunov (Kaplan-Yorke) dimensions and Komolgorov Sinai Entropy values based on RR Interval data derived form the electrocardiogram data. The chaos metric module 960 transmits the chaos metrics to the diagnosis module 920.

The mutual information module 950 generates information theory metrics such as entropy, conditional entropy and mutual information based on the electrocardiogram data associated with a subject. The mutual information module 950 can generate any type of information theory metric using correlation analyses such as the canonical correlation analyses described above. In some embodiments, the mutual information module 950 generates Shannon differential entropy values based on the series of RR intervals and the series of QT intervals. In a specific embodiment, the mutual information module 950 generates Kolmogorov-Sinai mutual information metrics based on the series of RR intervals and QT intervals derived form the electrocardiogram data. In this embodiment, Komolgorov-Sinai mutual information metrics are calculated in order to generate a value MI(QT->RR) which quantifies an amount by which the uncertainty in future RR intervals in the series of RR intervals is reduced based on the past QT interval data and a value MI(RR->QT) which quantifies an amount by which the uncertainty in the future QT intervals in the series of QT intervals is reduced based on the past RR interval data. The mutual information module 950 transmits the information theory metrics to the diagnosis module 920.

The Erlang fitting module 940 generates coefficients which describe how well a histogram of RR intervals derived from a subject's electrocardiogram data fit an Erlang distribution. The Erlang fitting module 940 can generate any value that describes the fit of the histogram to the Erlang distribution. In a specific embodiment, the Erlang fitting module 940 generates a chi-squared value that describes the likelihood that the RR Interval histogram would fit the Erlang distribution by chance as a coefficient. In another specific embodiment the Erlang fitting module 940 further generates parameters to describe the best Erlang distribution for the data as described above. The Erlang fitting module 940 transmits the coefficients to the diagnosis module 920.

The recurrence module 970 functions to generate stationarity value which characterize the stationarity of the electrocardiogram data. The recurrence module 970 generates stationarity values based on RR interval data according to stationarity metrics such as Poincare meta-recurrence metrics and Dickey-Fuller Root of Unity. The recurrence module 970 transmits the stationarity value to the diagnosis module 920.

The visualization module 930 generates interfaces for displaying the electrocardiogram data, the generated metrics and the risk of cardiac dysfunction on the display 218 of the client 150 and/or the heart health prediction server 110. The visualization module 930 generates plots of the generated metrics as described above. The visualization module 930 further generates displays of the generated metrics as compared to the threshold values used by the diagnostic module 920 to determine whether the subject is associated with a high or low risk for cardiac dysfunction. These displays allow a user of the visualization module 930 to qualitatively assess a subject's risk of cardiac dysfunction based on the generated metrics.

Figure 10:
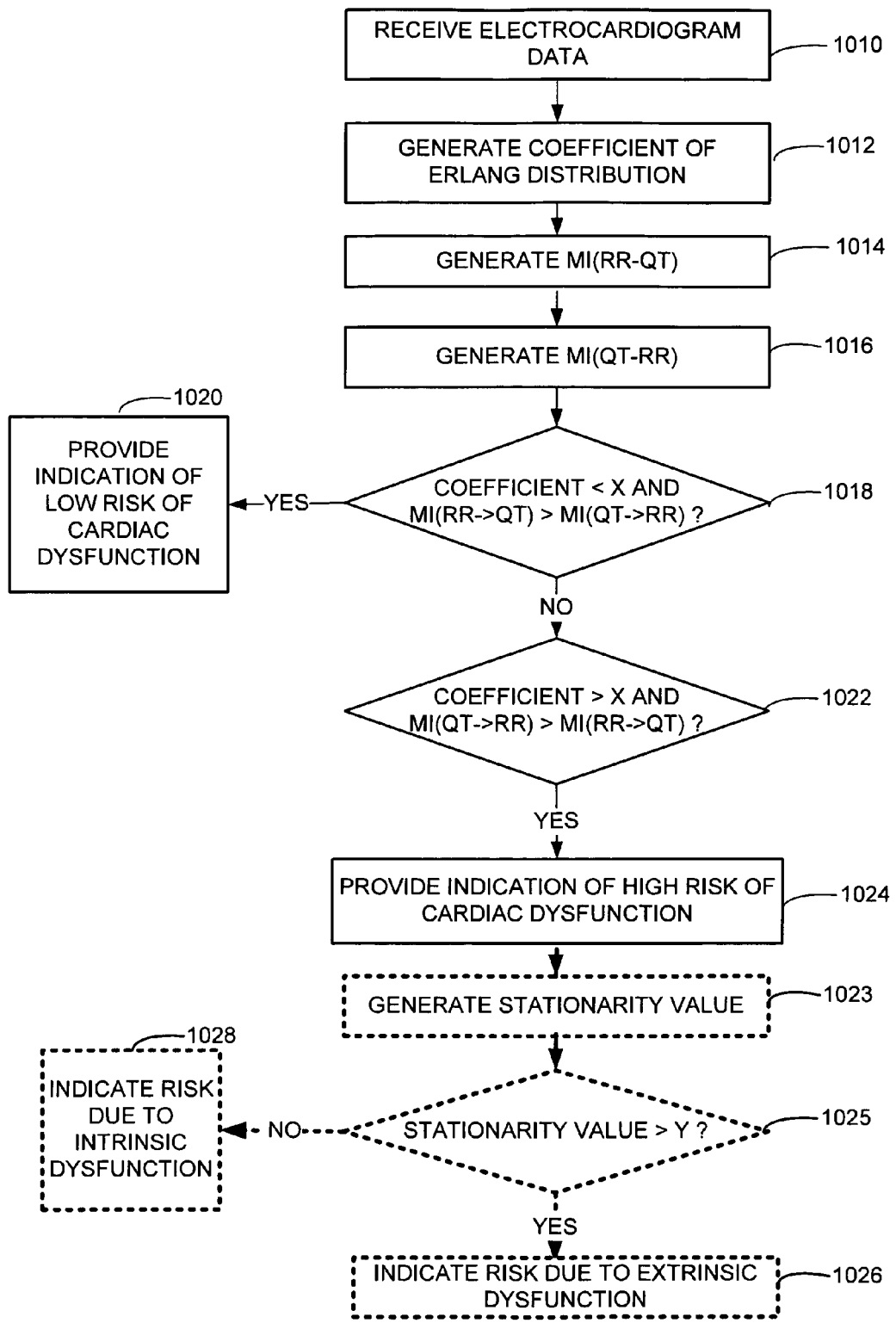
FIG. 10 is a flow chart illustrating steps performed by the heart health prediction server to determine a risk of cardiac dysfunction based on electrocardiogram data.

FIG. 10 is a flow chart illustrating steps performed by the heart health prediction server 110 to diagnose a risk of cardiac dysfunction based on electrocardiogram data.

The heart health prediction server 110 receives 1010 electrocardiogram data, including a series of RR intervals and a series of QT intervals. The heart health prediction server 110 generates 1012 a coefficient value which quantifies the fit of the RR intervals to the Erlang distribution. The heart health prediction server 110 generates 1014 a first value MI(RR->QT) which indicates an amount by which uncertainty in future QT intervals of the series of QT intervals is reduced by knowing the past RR interval data. The heart health prediction server 110 generates 1016 a second value MI(QT->RR) which indicates an amount by which the uncertainty in future RR intervals of the series of RR intervals is reduced by knowing the past QT interval data. The heart health prediction server 110 determines 1018 whether the fitting coefficient is below a threshold value X and whether the first value MI(RR->QT) is greater than the second value MI(QT->RR). If the coefficient is below the threshold value X and the first value MI(RR->QT) is greater than the second value MI(QT->RR), the heart health prediction server 110 determines that the subject is associated with a lower risk of cardiac disease and/or dysfunction and provides 1020 an indication of a low risk of cardiac dysfunction. If the coefficient exceeds the threshold value X and/or the first value MI(RR->QT) is not greater than the second value MI(QT->RR), the heart health prediction server 110 determines 1022 whether the coefficient is above a threshold value and whether the second value MI(QT->RR) is greater than the first value MI(RR->QT). If the coefficient exceeds the threshold value and the second value MI(QT->RR) is greater than the first value MI(RR->QT), the heart health system 110 determines that the subject is associated with a high risk of cardiac disease and/or dysfunction and provides 1024 an indication of a high risk of cardiac dysfunction.

In some embodiments, the heart health prediction server 110 generates 1023 a stationarity value responsive to determining that the subject is associated with a high risk of cardiac dysfunction. The heart health prediction server 110 determines 1025 whether the stationarity value exceeds a threshold value y. If the heart health prediction server 110 determines 1025 that the stationarity value exceeds a threshold value y, the heart health prediction server 110 provides 1026 an indication of risk of extrinsic cardiac dysfunction. If the heart health prediction server 110 determines 1025 that the stationarity value does not exceed the threshold value y, the heart health prediction server 110 provides 1028 an indication of risk of cardiac dysfunction due to intrinsic dysfunction.

The above description is included to illustrate to a client 150 according to one embodiment. Other embodiments the operation of certain embodiments and is not meant to limit the scope of the invention. The scope of the invention is to be limited only by the following claims. From the above discussion, many variations will be apparent to one skilled in the relevant art that would yet be encompassed by the spirit and scope of the invention.

Clinical Data:

The data analyzed in this research is from randomized, double blind, 5-way crossover. There were two data sets incorporated into the analysis, data from a phase 1 clinical drug trial and data from normal subjects (i.e. subjects with no known cardiac dysfunction). There were 12 subjects included in the phase 1 clinical drug trail data set. All 12 subjects gave informed consent to the pharmaceutical company that allowed the data for use. 11 of the 12 subjects had 5 electrocardiogram recordings, one subject had 4 electrocardiogram recordings. The electrocardiogram recordings were taken in randomized order at baseline (untreated with drugs), placebo, low-dose, medium dose and high-dose drug consumption. The original use of the data was to evaluate a sodium-channel blocker for arrhythmias and cardiac dysfunction which induced RR interval prolongation. The sodium-channel blocker is no longer being developed. Data sets include the 24-hour measurement of RR and QT intervals. There were also 66 data sets from normal subjects.

Lyapunov Exponents:

For a dynamical system, sensitivity to initial conditions is quantified by the Lyapunov exponents. The Lyapunov exponent is a quantitative measure of separation the trajectories that diverge widely from their initial close positions. There are as many Lyapunov exponents as there are dimensions in the state space of the system, but the largest is usually the most important. The magnitude of this exponent is proportional to how chaotic the system is. For periodic signals, the Lyapunov exponent is zero. A random signal will also have an exponent of zero. A positive Lyapunov exponent indicates sensitive dependence on the initial conditions and is diagnostic of chaos, although these exponents are not easily measured. The flow map:

$$\Phi^t: \mathbb{R}^n \to \mathbb{R}$$
$$x \mapsto \Phi^t(x)$$

describing the dynamical system acts on the n-dimensional state space $M = \mathbb{R}^n$ and is generate by vector field v:

$$\dot{x} = v(x), x \in \mathbb{R}^n, t \in \mathbb{R}$$

To gather information about the time evolution of infinitesimally small perturbed initial states, the linearized flow map has to be considered.

$$D_x\Phi^t: T_xM \to T_{\Phi^t(x)}M$$
$$u \mapsto D_x\Phi^t u$$

The linearized flow map $D_x\Phi^t$ is given by an invertible n×n matrix describing the time evolution of a vector u in tangent space. For ergodic systems the Lyapunov exponents are defined as the logarithms of the eigenvalues $\mu_i$ ($1 \leq i \leq m$) of the positive and symmetric limit matrix.

$$\Lambda_x = \lim_{t\to\infty}[D_x\Phi^{t*}D_x\Phi^t]^{\frac{1}{2t}}$$

as given by the theorem of Oseledec. The Lyapunov exponents are the logarithmic growth rates $$\lambda_i = \lim_{t\to\infty}\frac{1}{t}\ln\|D_x\Phi^t e_i\|, \quad (1 \leq i \leq m)$$

where $\{e_i: 1 \leq i \leq m\}$ are basis vectors that span the eigenspaces of $\Lambda_x$.

Any continuous time-dependent dynamical system without a fixed point will have at least one zero exponent, corresponding to the slowly changing magnitude of a principal axis tangent to the flow. The sum of the Lyapunov exponents is the time-averaged divergence of the phase space velocity; hence any dissipative dynamical system will have at least one negative exponent, the sum of all of the exponents is negative, and the post transient motion of trajectories will occur on a zero volume limit set, an attractor. The exponential expansion indicated by a positive Lyapunov exponent is incompatible with motion on a bounded attractor unless some sort of folding process merges widely separated trajectories. Each positive exponent reflects a direction in which the system experiences the repeated stretching and folding that decorrelates nearby states on the attractor. Therefore, the long-term behavior of an initial condition that is specified with any uncertainty cannot be predicted; this is chaos. An attractor for a dissipative system with one or more positive Lyapunov exponents is said to be strange or chaotic.

For time series produced by dynamical systems, the presence of a positive characteristic exponent indicates chaos. Recognizing that the length of the first principal axis is proportional to $e^{\lambda_1 t}$ the area determined by the first two principal axes is proportional to $e^{(\lambda_1+\lambda_2)t}$; and the volume determined by the first k principal axes is proportional to: $e^{(\lambda_1+\lambda_2+\ldots+\lambda_k)t}$. Thus, the Lyapunov spectrum can be defined such that the exponential growth of a k-volume element is given by the sum of the k largest Lyapunov exponents. Note that information created by the system is represented as a change in the volume defined by the expanding principal axes.

In a geometrical point of view, to obtain the Lyapunov spectra, imagine an infinitesimal small ball with radius dr sitting on the initial state of a trajectory. The flow will deform this ball into an ellipsoid. That is, after a finite time t all orbits which have started in that ball will be in the ellipsoid. The $i^{th}$ Lyapunov exponent is defined by:

$$\lambda_i = \lim_{t\to\infty}\frac{1}{t}\left(\frac{dl_i(t)}{dr}\right)$$

where $dl_i(t)$ is the radius of the ellipsoid along its $i^{th}$ principal axis 2.4)).

The separation must be measures along the Lyapunov directions which correspond to the principal axes of the ellipsoid previously considered. These Lyapunov directions are dependent upon the system flow and are defined using the Jacobian matrix, i.e., the tangent map, at each point of interest along the flow. Hence, one must preserve the proper phase space orientation by using a suitable approximation of the tangent map. This requirement, however, becomes unnecessary when calculating only the largest Lyapunov exponent. If we assume that there exists an Ergodic measure of the system, then the multiplicative Ergodic theorem of Oseledec justifies the use of arbitrary phase space directions when calculating the largest Lyapunov exponent with smooth dynamical systems. This is due to the fact that chaotic systems are electively stochastic when embedded in a phase space that is too small to accommodate the true dynamics.

In Ergodic systems most trajectories will yield the same Lyapunov exponent, asymptotically for long times. The computation of the full Lyapunov spectrum requires considerably more effort than just the maximal exponent. An essential ingredient is some estimate of the local Jacobians, i.e., of the linearized dynamics, which rules the growth of infinitesimal perturbations. One either finds it from direct fits of local linear models of the $s_{n+1}=a_n s_n + b_n$, such that the first row of the Jacobian is the vector $a_n$, and $(J)_{i,j}=\delta_{i-1,j}$ for $i=2, \ldots m$, where m is the embedding dimension. The $a_n$ is given by the least squares minimization $$\sigma^2 = \sum_l (s_{l+1} - a_n s_l - b_n)^2$$

where $\{s_i\}$ is the set of neighbors of $s_n$. Or one constructs a global nonlinear model and computes its local Jacobians by taking derivatives. In both cases, one multiplies the Jacobians one by one, following the trajectory, to as many different vectors $u_k$ in tangent space as one wants to compute Lyapunov exponents. Every few steps, one applies a Gram-Schmidt orthonormalization procedure to the set of $u_k$, and accumulates the logarithms of their rescaling factors. The average of these values, in the order of the Gram-Schmidt procedure, give the Lyapunov exponents in descending order. The routine used in this research, "lyap_spec", uses this method of employing local linear fits. This routine is described in detail on pgs. 329-334 of Provisional Application 61/062,366.

Kolmogorov-Sinai Entropy:

The Kolmogorov-Sinai Entropy metric measures how chaotic an experimental signal is. In the case of deterministic chaos, K is positive and measures the average rate at which the information about the state of the system is lost over time. In other words, K is inversely proportional to the time interval over which the state of the system can be predicted. Moreover, K is related to the sum of the positive Lyapunov exponents. The Kolmogorov-Sinai entropy can be evaluated quantitatively and is diagnostic of chaos, whereas some other methods such as spectral analysis, time autocorrelation function and scatter plot construction are qualitative methods.

As an approximation, the sum of the corresponding exponents (i.e., the positive exponents), equals the Kolmogorov entropy (K) or mean rate of information gain:

$$K = \sum_{\lambda_i > 0} \lambda_i$$

Lyapunov (Kaplan-Yoke) Dimension:

Lyapunov dimension is another Fractal dimension, introduced by Kaplan and Yorke based on the Lyapunov exponents. If $\Phi^t$ is a map on $\mathbb{R}^n$ and $O_\Phi^+(x_0)$ is a bounded forward orbit having Lyapunov exponents $\lambda_j = \lambda_j(x_0; \Phi)$ with, for the integer k such that:

$\lambda_1 + \lambda_2 + \ldots + \lambda_k \geq 0$
$\lambda_1 + \lambda_2 + \ldots + \lambda_{k+1} < 0$ then, the Lyapunov Dimension of the orbit is $$dim_L(O_\Phi^+(x_0)) = k + \frac{\sum_{i=1}^k \lambda_i}{|\lambda_{k+1}|}$$

Notice that $\lambda_1 + \lambda_2 + \ldots + \lambda_k < |\lambda_{k+1}|$ so $dim_L(O_\Phi^+(x_0)) < k+1$. If the attractor has a positive Lyapunov exponent, then $k \geq 1$. The fractal dimensions of chaotic flows are shown to be given $D = m^0 + m^+ \{1 + |\lambda^+/\lambda^-|\}$, where $m^0$ and $m^+$ are the numbers of zero and positive Lyapunov characteristic exponents $\lambda_\alpha$ and $\lambda^\pm$ are the mean values of positive and negative $\lambda_\alpha$ respectively.

Canonical Correlation Analysis:

Canonical Correlation Analysis (CCA) is a second moment technique. Therefore, it is not suitable for the systems with infinite variance, such as self-similar signals or highly noisy data, in its linear version; however, in the nonlinear version, this is not the issue. In the nonlinear CCA, since the variance analysis is applied to a nonlinear distortion of the original process, which is restricted to result in a finite variance process.

Assume that time series $\{y(k): k=\ldots, -1, 0, 1, \ldots\}$ is a centered process, bounded and viewed as weakly stationary process with finite covariance $E(y(i)y(j))=\Lambda_{i-j}$ defined over the probably space $(\Omega, A, \mu)$. If the process is not stationary, we can simply compute $z(k)=y(k)-y(k-1)$, which is usually stationary. The past and the future of the process are defined, respectively as:

$y_-(k)=(y(k), y(k-1), y(k-2), \ldots, y(k-L+1))^T$ $y_+(k)=(y(k+1), y(k+2), y(k+3), \ldots, y(k+L))^T$ where L is the lag. Interrelation between past and the future is as a preliminary study of whether a recipe of the form $y_+ = f(y_-)$ is likely to work. The ability to devise a good model can be gauged from the Kolmogorov-Sinai, or Shannon, mutual information between the past and the future. The mutual information between the past $y_-$ and the future $y_+$ is the amount by which the Shannon entropy of the future decreases the past is given; that is, $$I(y_-, y_+) = h(y_+) - h(y_+ | y_-)$$
$$= \int \int \log \frac{p(y_-, y_+)}{p(y_-)p(y_+)} p(y_-, y_+) dy_- dy_+$$

In the above equation, $h(y_+)$ is the Shannon entropy of the future and $h(y_+|y_-)$ is the conditional entropy of the future given the past.

Linear Canonical Correlation Analysis:

In the linear version of CCA, the best linear regression between the past and the future data is sought. In this regard and to proceed from a numerical algebra point of view, the covariance of the past and the future are factored as $E(y_-(k) y_-^T(k)) = C_{--} = L_-^T L_-$ $E(y_+(k) y_+^T(k)) = C_{++} = L_+^T L_+$ where $L_-$ and $L_+$ are Cholesky factorization of the past and future, respectively. $C_{--}$ and $C_{++}$ are Toeplitz matrices and measures of strength of the past and the future, respectively. These quantities are used for normalization to get the information interface, independently of the strength of the signals.

Therefore the canonical correlation is defined as:

$$\Gamma(y_-, y_+) = L_-^{-T} E(y_-(k), y_+^T(k)) L_+^{-1}$$

which asymptotically is a Hankel matrix in the case of large data records. The Singular Value Decomposition (SVD) of the canonical correlation matrix is given as $\Gamma(y_-(k), y_+(k)) = U\Sigma V^T$ where U and V are orthogonal matrices:

$$\Sigma \begin{pmatrix} \sigma_1 & \cdots & 0 \\ \vdots & \ddots & \vdots \\ 0 & \cdots & \sigma_L \end{pmatrix}, \quad 1 \geq \sigma_1 \geq \ldots \geq \sigma_L \geq 0$$

The $\sigma_i$'s are called canonical correlation coefficients (CCC's) and are invariant under the nonsingular linear transformations of the past and the future. For the Gaussian processes it is well known that:

$$I(y_-, y_+) = -\frac{1}{2} \log(\det(I - \Sigma^2))$$

wherein the right hand side of the question represents the maximum information that can be achieved.

It is claimed that there are only restricted number $D \leq L$ of significant CCC's, grouped in $\Sigma_1$. Hence, matrices $\Sigma$, U, and V are partitioned. The canonical past and the canonical future are defined as:

$$\bar{y}_-(k) = U_1 L_-^{-T} y_-(k)$$

$$\bar{y}_+(k) = V_1 L_+^{-1} y_+(k)$$

The state is defined as the minimum collection of past measurable random variables necessary to predict the future, that is, $E(\bar{y}_+(k) | \bar{y}_-(k))$. The state space model can be defined as:

$$x(k+1) = Fx(k) + w(k)$$

where w(k) is desired to be white noise and $x(k) = \Sigma_1 \bar{y}_-(k)$. F is the regression matrix of x(k+1) on x(k) and for the best prediction it is defined as:

$$F = E\{x(k+1)x^T(k)\}(E\{x(k)x^T(k)\})^{-1}$$

and the residual error is:

$$E\{[x(k+1) - Fx(k)][x(k+1) - Fx(k)]^T\} \sim (I - \Sigma_1^2)$$

Non-linear Canonical Correlation Analysis:

In nonlinear canonical correlation, a nonlinear processing is done on the past and the future. This is the case in which the maximum possible mutual information is attempted to reach. In general (non-Gaussian setup):

$$\sup_{f,g} I(f(y_-), g(y_+)) \leq I(y_-, Y_+)$$

where $f, g: \mathfrak{R}^L \to \mathfrak{R}^L$ are measurable, objective functions such that $E(f) = E(g) = 0$, $E(ff^T) < \infty \times I$, where I is the identity matrix. Equality is achieved if and only if $f(y_-), g(y_+)$ can be made jointly Gaussian. In this case the linear estimation $\hat{g}(y_+) = Af(y_-)$ is optimum. In fact, components of $f(y_-), g(y_+)$ can be expressed as linear combination of functions $p_j(y_-), q_j(y_+)$, j=1, 2, . . . , such that $E_-(p_j) = E_+(q_j) = 0$, $E_-(pp^T) < \infty \times I$ and $E_+(qq^T) < \infty \times I$, and forming basis of the Lebesgue spaces of zero mean measurable functions such that $E_- ff^T < \infty$ and $E_+ g^T g < \infty$, respectively. For $L < \infty$, the same procedure as the linear case is followed and canonical correlation matrix $\Gamma(p(y_-), q(y_+))$ is computed.

The motivation for the nonlinear processing of the data is to gauge in comparison with the full dimensional linear case, how much increase in CCC's is gained by going to the nonlinear analysis. Observation of increased information indicates the nonlinearity of the process.

Consider that $f(y_-), g(y_+)$ are jointly Gaussian functions, it can be found that:

$$\min_A E\|g(y_+) - Af(y_-)\|_{C_{++}^{-1}}^2 = L - \text{Trace}(\Gamma^T \Gamma(f(y_-), g(y_+)))$$

for $$A = \Sigma_{f(y_-), g(y_+)}.$$

It is claimed that:

$$f(y_-) = U_1^T L_-^{-T} p(y_-)$$

$$g(y_+) = V_1 L_+^{-1} q(y_+)$$

where $U_1$ and $V_1$ are computed from factorization of the SVD of the nonlinear canonical correlation matrix. The state space model is constructed following the same procedure as in the linear case.

REFERENCES

H. Akaike. A new look at the statistical model identification. IEEE Transaction on Automatic Control, AC-19(6):716-723, December 1974.

L. Arnold, H. Crauel, and J. P. Ekmann, editors. Lyapunov Exponents, Berlin Heidelberg, 1991. Springer-Verlag.

R. Barbieri and E. N. Brown. Analysis of heart beat dynamics by point process adaptive filtering. IEEE Transaction On Biomedical Engineering, 53(1), January 2006.

S. Bohacheck and E. Jonckheere. Linear dynamically varying H-infinity control of chaos. Nonlinear Control System Design Symposium (NOLCOS 1998), pages 745-750, 1998.

L. Breiman and J. H. Friedman. Estimating optimal transformations for multiple regression and correlation. Journal of the American Statistical Association, 80(391):580-598, September 1985.

R. Brown, P. Bryant, and H. D. I. Abarbanel. Computing the Lyapunov spectrum of a dynamical system from an observed time series. Physical Review A, 43(6), 1991.

A. Casaleggio, S. Cerutti, and G. Signorini. Study of the Lyapunov exponents in heart rate variability signals. Methods of Information in Medicine, 36(4-5):274-7, December 1997.

B. Choi. ARMA Model Identification. Springer-Verlag, 1992.

J. L. Doob. Stochastic Processes. John Wiley and Sons, 1953.

B. Eckhardt and D. Yao. Local Lyapunov exponents in chaotic systems. Physica D, 65:100-108, 1993.

J. P. Eckmann, D. Ruelle S. O. Kamphorst, and S. Ciliberto. Lyapunov exponents from time series. Physical Review A, 34(6), 1986.

A. U. Rajendra et al. Heart rate analysis in normal subjects of various age groups. BioMedical Engineering OnLine, 3:24 doi:10.1186/1475-925X-3-24, 2004.

M. A. Van Ravenswaaij-Arts et al. Heart rate variability. Annals of Internal Medicine, 118(6):436-47, March 1993.

R. E. Kleiger et al. Decreased heart rate variability and its association with increased mortality after acute myocardial infraction. The American Journal of Cardiology, 59(4): 256-2, February 1987.

T. Elbert et al. And physiology: Deterministic chaos in excitable cell assemblies. Physical Reviews, 74(1), 1994.

D. Faller. Analysis and Dynamic Modeling of Complex Systems. PhD thesis, Albert "ULudwigs"UUniversität Freiburg im Breisgau, 2003.70

J. O. Fortrat, Y. Yamamoto, and R. L. Hughson. Respiratory influences on non-linear dynamics of heart rate variability in humans. Biol. Cybern., 77:1-10, 1997.

P. Grassberger and I. Procaccia. The strangeness of strange attractors. Physica 9D, (9):189-208, 1983.

H. Haken. At least one Lyapunov exponent vanishes if the trajectory of an attractor does not contain a fixed point. Phys. Lett. A, 94:71, 1983.

J. R. Hampton. The ECG Made Easy. Churchill Livingstone, sixth edition, 2003.

E. Hashida and T. Tasaki. Considerations on the nature of irregularity of the sequence of RR intervals and the function of the atrioventricular node in atrial fibrillation in man based on time series analysis. Japanese Heart Journal, 25(5):669-687, September 1984.

N. Haydn. The limiting distribution and error terms for return times of dynamical systems. Discrete and Continuous Dynamical Systems, 10(3):589-616, April 2004.

N. Haydn and S. Vaienti. Fluctuations of the metric entropy for mixing measures. Stochastics and Dynamics, 4(4):595-627, 2004.

R. Hegger, H. Kantz, and T. Schreiber. Practical implementation of nonlinear time series methods: The TISEAN package. Chaos, 9:413, 1999.

R. A. Holmgren. A First Course in Discrete Dynamical Systems. Springer-Verlag, second edition, 1996.

J. D. and C. T. MacArthur. Research network on socioeconomic status and health. 1986.

Javier Jo. Linear and Nonlinear Model-Based Assessment of Autonomic Control in Obstructive Sleep Apnea Syndrome (OSAS) During Wakefulness and Sleep. PhD thesis, University of Southern California, 2002.71

E. Jonckheere. Chaotic systems. Lecture Notes, Chaotic Systems course (EE584), Department of Electrical Engineering-Systems, University of Southern California, 2006.

Wallace E. Larimore. System identification and filtering of nonlinear controlled markov processes by canonical variate analysis. Technical report, Air Force Office of Scientific Research Bolling AFB, DC, October 1989.

C. Lerma, O. Infante, H. Perez-Grovas, and M. V. Jose. Poincare plot indexes of heart rate variability capture dynamic adaptations after haemodialysis in chronic renal failure patients. Clin Physiol and Func Im, 23:72-80, 2003.

P. Lohsoonthom and E. Jonckheere. Nonlinear switching dynamics in surface electromyography of the spine, Conference on Physics and Control, St. Petersburg, Russia, August 2003. pages 276-281.

M. Malik. Heart rate variability. Current Opinion in Cardiology, 13(1):36-44, January 1998.

P. E. McSharry, G. D. Cliord, L. Tarassenko, and L. A. Smith. A dynamical model for generating synthetic electrocardiogram signals. IEEE Transaction on Biomedical Engineering, 50(3), March 2003.

H. Mori. Fractal dimensions of chaotic flows of autonomous dissipative systems. Progress of Theoretical Physics, 63(3): 1044-1047. 72

K. Narayanan, R. B. Govindan, and M. S. Gopinathan. Unstable periodic orbits in human cardiac rhythms. Phys Rev E, 57:4594-4603, 1998.

V. I. Oseledec. A multiplicative ergodic theorem: Lyapunov characteristic numbers for dynamical systems. Trans. Moscow Math. Soc., 19:197-231, 1968.

D. Pena, G. C. Tiao, and R. S. Tsay. A Course in Time Series Analysis. John Wiley and Sons, 2001.

R. C. Robinson. An Introduction to Dynamical Systems: Continuous and Discrete. Pearson. Prentice Hall, 2004.

M. T. Rosenstein, J. J. Collins, and C. J. De Luca. A practical method for calculating largest Lyapunov exponents from small data sets. Physica D, 65:117-134, 1993.

M. Sakki, J. Kalda, M. Vainu, and M. Laan. What does measure the scaling exponent of the correlation sum in the case of human heart rate? arXiv:physics/0112031, 2(8), January 2003.

M. Sano and Y. Sawada. Measurement of the Lyapunov spectrum from a chaotic time series. Phys. Rev. Lett., 55:1082, 1985.

S. Bohacek and E. Jonckheere, "Chaotic modeling in Network Spinal Analysis: Nonlinear Canonical Correlation with Alternating Conditional Expectation (ACE): A preliminary report," in *Journal of Vertebral Subluxation Research*, vol. 2(4), pp. 188-195, December 1998.

K. Shah, E. Jonckheere, and S. Bohacek. Dynamic modeling of internet traffic: Linear versus nonlinear canonical correlation analysis of HTTP versus FTP traffic. Technical Report, Department of Electrical Engineering—Systems, University of Southern California, Los Angeles, Calif., December 2001. (See http://eudoxus.usc.edu/CHAOS/HTTPvsFTP.pdf.)

K. Shah and E. A. Jonckheere, Dynamic modeling of Internet traffic, *National Science Foundation Southwest Regional Workshop on New Directions in Dynamical Systems*, University of Southern California, Los Angeles, Calif., Nov. 16-19, 2000. (see http://eudoxus.usc.edu/CHAOS/dynamicsnew.pdf)

E. A. Jonckheere and A. Hammad, "Taming Chaos—A numerical experiment using LTI filters," *IEEE Transactions on Circuits and Systems*, vol. CAS-42, pp. 111-115, February 1995.

A. Hammad, E. A. Jonckheere, C.-Y. Cheng, S. Bhajekar, and C.-C. Chien, "Stabilization of chaotic dynamics—A modern control approach," *International Journal on Control*, vol. 64, Number 4, pp. 663-677, July 1996.

K. Shah, E. Jonckheere, and S. Bohacek. Dynamic modeling of Internet traffic for intrusion detection. EURASIP Journal on Advances in Signal Processing, 2007:1-14, 2007; article ID 90312; doi:10.1155/2007/90312.

M. Small. Applied Nonlinear Time Series Analysis, volume 52 of A. World Scientific, 2005.

M. S. Thaler. The Only EKG Book You'll Ever Need. Lippincott Williams and Wilkins, 4th edition, 2003.

C. D. Wagner and P. B. Persson. Chaos in the cardiovascular system: An update. Cardiovascular Research, 40:257-264, 1998.

D. Wang and M. Murphy. Estimating optimal transformations for multiple regression using the ACE algorithm. Journal of Data Science, 2:329-346, 2004.

A. Wolf, J. B. Swift, H. L. Swinney, and J. A. Vastano. Determining Lyapunov exponents from a time series. Physica D, 16:285-317, 1985.

B. F. Wu. Identification and Control of Chaotic Processes—The Kolmogrov-Sinai Entropy Approach. Ph.D. thesis, Department of Electrical Engineering—Systems, University of Southern California, 1992.

E. A. Jonckheere and B.-F. Wu, "Chaotic disturbance rejection and Bode limitation," *American Control Conference*, Chicago, Ill., Jun. 24-26, 1992, TP1, pp. 2227-2231.

E. A. Jonckheere and Bing-Fei Wu, "Mutual Kolmogorov-Sinai entropy approach to nonlinear estimation," *IEEE Conference on Decision and Control*, Tucson, Ariz., December 1992, pp. 2226-2232.

N. Haydn and E. Jonckheere, "On mutual information", to be submitted, 2005.

D. C. Michaels, E. P. Matyas, and J. Jalife. Mechanisms of sinoatrial pacemaker synchronization: A new hypothesis. Circulation Research, 61(5):704-714, November 1987.

C. S. Poon, M. Barahona. "Titration of chaos with added noise." *Proc Natl Acad Sci USA*, 2001; 98:7107-7112

C. S. Poon, C. K. Merrill, "Decrease of cardiac chaos in congestive heart failure." *Nature,* 1997; 389:492-495

M. Barahona, C. S. Poon, "Detection of nonlinear dynamics in short, noisy data." *Nature,* 1996; 381:215-217

APPENDIX A

Normal Subject Metrics

| Index (Normal No.) | Lyapunov Exponents | Estimated Kolmogorov Entropy | Estimated Kaplan-Yorke Dimension | Goodness of Erlang Fit (LSE) |
|---|---|---|---|---|
| 1 | 0.4626789<br>0.0035272<br>−0.6517636 | 0.466206 | 2.715300 | 2.67E−06 |
| 2 | 0.2895753<br>−0.0888379<br>−0.6927569 | 0.289575 | 2.289766 | 2.12E−05 |
| 3 | 0.4603707<br>−0.0324804<br>−0.7059873 | 0.460371 | 2.606088 | 2.14E−05 |
| 4 | 0.4656253<br>−0.0236436<br>−0.6975281 | 0.465625 | 2.633640 | 8.87E−06 |
| 5 | 0.4693237<br>0.0017717<br>−0.650464 | 0.471095 | 2.724245 | 1.94E−05 |
| 6 | 0.4437319<br>−0.0079419<br>−0.6453073 | 0.443732 | 2.675322 | 8.11E−06 |
| 7 | 0.4294281<br>0.0002305<br>−0.6402668 | 0.429659 | 2.671062 | 4.86E−06 |
| 11 | 0.4412964<br>−0.02450989<br>−0.6856878 | 0.441296 | 2.607837 | 6.11E−06 |
| 12 | 0.4110762<br>−0.0404962<br>−0.6729402 | 0.411076 | 2.550688 | 1.97E−05 |
| 13 | 0.296361<br>−0.1145268<br>−0.7154075 | 0.296361 | 2.254169 | 5.77E−05 |
| 14 | 0.3736964<br>−0.06247597<br>−0.692537 | 0.373696 | 2.449392 | 7.54E−06 |
| 15 | 0.4061888<br>−0.0357784<br>−0.6770191 | 0.406189 | 2.547120 | 1.14E−05 |
| 16 | 0.3776069<br>−0.0789358<br>−0.7294197 | 0.377607 | 2.409464 | 1.58E−05 |
| 17 | 0.4122025<br>−0.0352633<br>−0.6684468 | 0.412203 | 2.563903 | 1.23E−05 |
| 18 | 0.3881749<br>−0.0635190<br>−0.6913329 | 0.388175 | 2.469609 | 1.25E−06 |
| 19 | 0.4429376<br>−0.0078992<br>−0.6630221 | 0.442938 | 2.656145 | 4.16E−06 |
| 20 | 0.4855205<br>−0.0188687<br>−0.7007498 | 0.485521 | 2.665932 | 1.57E−05 |
| 21 | 0.2955212<br>−0.0914378<br>−0.6720979 | 0.295521 | 2.303651 | 2.86E−05 |
| 22 | 0.4507159<br>−0.0272657<br>−0.6764186 | 0.450716 | 2.626018 | 6.80E−05 |
| 23 | 0.4257192<br>−0.0170116<br>−0.6356794 | 0.425719 | 2.642946 | Inf |

APPENDIX A-continued

| | | Normal Subject Metrics | | |
|---|---|---|---|---|
| Index (Normal No.) | Lyapunov Exponents | Estimated Kolmogorov Entropy | Estimated Kaplan-Yorke Dimension | Goodness of Erlang Fit (LSE) |
| 24 | 0.4064944<br>−0.0329571<br>−0.6683800 | 0.406494 | 2.558870 | 1.39E−05 |
| 25 | 0.3205683<br>−0.0992338<br>−0.6921756 | 0.320568 | 2.319766 | 1.92E−05 |
| 26 | 0.4248038<br>−0.0174760<br>−0.6580406 | 0.424804 | 2.619001 | 2.57E−06 |
| 27 | 0.4383994<br>−0.0359339<br>−0.6870821 | 0.438399 | 2.585760 | 2.29E−05 |
| 28 | 0.4483487<br>−0.0266034<br>−0.6838431 | 0.448349 | 2.616728 | 1.99E−05 |
| 29 | 0.4935920<br>−0.0063782<br>−0.6729682 | 0.49359 | 2.723977 | 6.25E−07 |
| 30 | 0.4301225<br>−0.0157002<br>−0.6571100 | 0.43012 | 2.630674 | 3.19E−05 |
| 31 | 0.4838183<br>0.0025148<br>−0.6547033 | 0.48633 | 2.742830 | 2.05E−06 |
| 32 | 0.4495922<br>−0.0104394<br>−0.6580090 | 0.44959 | 2.667396 | 4.09E−06 |
| 33 | 0.5209759<br>0.0134498<br>−0.6581510 | 0.53443 | 2.812011 | 9.17E−06 |
| 35 | 0.4993124<br>0.0341490<br>−0.6146335 | 0.53346 | 2.867934 | 2.83E−06 |
| 36 | 0.4430250<br>−0.0331921<br>−0.6897429 | 0.44303 | 2.594182 | 4.78E−06 |
| 37 | 0.5016889<br>0.0301184<br>−0.6340905 | 0.53180725 | 2.838693 | 1.13E−05 |
| 38 | 0.4992861<br>0.0244661<br>−0.6385589 | 0.52375215 | 2.820210 | 2.95E−06 |
| 39 | 0.4380424<br>−0.0036062<br>−0.6376166 | 0.4380424 | 2.681344 | 2.19E−06 |
| 40 | 0.5040903<br>0.0268242<br>−0.6308844 | 0.53091445 | 2.841540 | 6.73E−05 |
| 41 | 0.4820569<br>0.0259424<br>−0.6275755 | 0.50799932 | 2.809463 | 4.21E−06 |
| 42 | 0.4493009<br>−0.0026156<br>−0.6499468 | 0.4493009 | 2.687264 | 1.26E−06 |
| 43 | 0.5159200<br>0.0187411<br>−0.6536726 | 0.53466111 | 2.817934 | 4.15E−06 |
| 44 | 0.4867633<br>0.0156383<br>−0.6543973 | 0.50240156 | 2.767732 | 3.99E−06 |
| 45 | 0.5617581<br>0.0534298<br>−0.6246357 | 0.61518794 | 2.984875 | 1.94E−05 |
| 46 | 0.5403758<br>0.0294637<br>−0.6394360 | 0.5698395 | 2.891160 | 2.47E−06 |
| 47 | 0.5037656<br>0.0150261<br>−0.6515009 | 0.51879166 | 2.796302 | 8.71E−06 |
| 48 | 0.4261795<br>−0.0050270<br>−0.6335384 | 0.4261795 | 2.664762 | 9.70E−07 |

APPENDIX A-continued

Normal Subject Metrics

| Index (Normal No.) | Lyapunov Exponents | Estimated Kolmogorov Entropy | Estimated Kaplan-Yorke Dimension | Goodness of Erlang Fit (LSE) |
|---|---|---|---|---|
| 49 | 0.5019840<br>0.0202694<br>−0.6382995 | 0.52225343 | 2.818195 | 4.12E−06 |
| 50 | 0.4603309<br>0.0131815<br>−0.6232286 | 0.47351243 | 2.759773 | 3.83E−06 |
| 51 | 0.4924856<br>0.0303060<br>−0.6171928 | 0.52279164 | 2.847047 | 1.55E−05 |
| 52 | 0.4739981<br>0.0033212<br>−0.6722974 | 0.477319276 | 2.709982 | 4.28E−06 |
| 53 | 0.5014370<br>0.0266734<br>−0.6275965 | 0.52811035 | 2.841481 | 1.34E−05 |
| 54 | 0.4136532<br>0.0074098<br>−0.6171979 | 0.421062986 | 2.682217 | 1.34E−05 |
| 55 | 0.4187179<br>−0.0031114<br>−0.6357596 | 0.4187179 | 2.653716 | 1.42E−05 |
| 56 | 0.4599587<br>0.0103607<br>−0.6493294 | 0.47031936 | 2.724315 | 1.44E−06 |
| 57 | 0.5225741<br>0.0385376<br>−0.6255116 | 0.5611117 | 2.897044 | 5.98E−06 |
| 58 | 0.6037701<br>0.0641090<br>−0.6158282 | 0.6678791 | 3.000000 | 4.39E−06 |
| 59 | 0.4336755<br>−0.0156398<br>−0.6519512 | 0.4336755 | 2.641207 | 6.60E−06 |
| 60 | 0.4231674<br>−0.0018768<br>−0.6296249 | 0.4231674 | 2.669113 | Inf |
| 61 | 0.4893115<br>0.0283230<br>−0.6219722 | 0.51763451 | 2.832247 | 1.09E−05 |
| 62 | 0.4627798<br>−0.0176291<br>−0.6813463 | 0.4627798 | 2.653340 | 1.90E−05 |
| 63 | 0.4560998<br>−0.0001225<br>−0.6495752 | 0.4560998 | 2.701962 | 3.53E−05 |
| 64 | 0.4923906<br>0.0025509<br>−0.6568578 | 0.49494146 | 2.753499 | 8.27E−06 |
| 65 | 0.4663177<br>−0.0073879<br>−0.6677395 | 0.4663177 | 2.687289 | 7.03E−06 |
| 66 | 0.4973051<br>0.0022770<br>−0.6625014 | 0.499582069 | 2.754085 | 6.42E−07 |

APPENDIX B

Normal Subject Mutual Information Metrics

| | Lag = 25 | | 50 | | 100 | | 500 | |
|---|---|---|---|---|---|---|---|---|
| No. | RR->QT | QT->RR | RR->QT | QT->RR | RR->QT | QT->RR | RR->QT | QT->RR |
| 1 | 15.494 | 15.523 | 29.832 | 31.438 | 53.797 | 62.634 | Inf | Inf |
| 2 | 21.542 | 21.139 | 28.95 | 30.965 | 38.353 | 37.997 | Inf | 75.867 |
| 3 | 15.152 | 14.409 | 28.136 | 29.754 | 57.01 | 55.707 | Inf | Inf |
| 4 | 17.442 | 14.73 | 33.804 | 35.58 | 62.51 | 67.738 | Inf | Inf |
| 5 | 15.308 | 14.371 | 28.614 | 27.839 | 62.234 | 63.077 | Inf | Inf |
| 6 | 15.069 | 13.361 | 26.51 | 26.979 | 57.697 | 61.65 | Inf | Inf |
| 11 | 14.333 | 15.603 | 28.76 | 29.251 | 55.762 | 60.377 | Inf | Inf |
| 12 | 14.297 | 14.833 | 29.634 | 30.203 | 59.385 | 57.915 | Inf | Inf |

APPENDIX B-continued

Normal Subject Mutual Information Metrics

| | Lag = 25 | | 50 | | 100 | | 500 | |
|---|---|---|---|---|---|---|---|---|
| No. | RR->QT | QT->RR | RR->QT | QT->RR | RR->QT | QT->RR | RR->QT | QT->RR |
| 13 | 29.493 | 31.514 | 35.93 | 39.696 | 51.198 | 56.266 | Inf | Inf |
| 14 | 13.888 | 14.226 | 26.668 | 28.524 | 58.862 | 59.221 | Inf | Inf |
| 15 | 15.988 | 14.697 | 29.137 | 29.764 | 57.545 | 61.634 | 279.49 | Inf |
| 16 | 14.986 | 13.677 | 50.659 | 57.023 | 72.731 | 79.507 | 238.28 | 245.48 |
| 17 | 17.187 | 13.657 | 34.307 | 32.542 | 62.039 | 61.796 | Inf | Inf |
| 18 | 15.157 | 15.207 | 29.013 | 35.504 | 58.481 | 68.675 | Inf | Inf |
| 19 | 27.585 | 31.309 | 49.565 | 39.698 | 52.016 | 58.674 | 167.81 | 218.92 |
| 20 | 16.606 | 15.783 | 32.699 | 19.927 | 64.8 | 53.081 | Inf | Inf |
| 21 | 17.65 | 15.874 | 34.963 | 31.032 | 58.756 | 71.279 | Inf | Inf |
| 22 | 13.473 | 14.867 | 25.146 | 30.104 | 51.323 | 58.519 | Inf | Inf |
| 23 | 15.052 | 14.81 | 30.699 | 27.967 | 56.789 | 67.423 | Inf | Inf |
| 24 | 13.98 | 14.477 | 26.9 | 26.726 | 53.245 | 56.105 | Inf | Inf |
| 25 | 15.427 | 17.456 | 31.82 | 29.071 | 65.263 | 62.13 | Inf | Inf |
| 26 | 16.063 | 16.939 | 28.185 | 26.55 | 55.842 | 57.396 | Inf | Inf |
| 27 | 12.874 | 13.797 | 30.468 | 30.838 | 71.212 | 83.572 | Inf | Inf |
| 28 | 14.31 | 14.942 | 27.641 | 27.597 | 60.383 | 55.061 | Inf | Inf |
| 29 | 12.636 | 14.629 | 26.895 | 27.023 | 54.9 | 54.374 | Inf | Inf |
| 30 | 14.232 | 14.667 | 28.629 | 29.023 | 53.35 | 56.553 | Inf | Inf |
| 31 | 14.127 | 22.248 | 27.517 | 34.603 | 48.933 | 63.713 | 304.25 | 290.55 |
| 32 | 13.093 | 14.176 | 31.072 | 28.786 | 61.055 | 57.016 | Inf | 263.93 |
| 33 | 14.635 | 14.501 | 26.413 | 28.015 | 56.384 | 53.871 | Inf | Inf |
| 34 | 16.475 | 16.161 | 29.314 | 29.01 | 51.882 | 53.227 | Inf | 280.95 |
| 35 | 14.337 | 14.717 | 28.683 | 26.948 | 61.841 | 57.41 | 278.26 | 274.36 |
| 36 | 16.198 | 13.306 | 31.21 | 31.34 | 61.19 | 60.076 | Inf | Inf |
| 37 | 15.24 | 14.08 | 27.27 | 27.102 | 54.756 | 57.952 | 291.98 | 276.74 |
| 38 | 15.522 | 13.675 | 29.125 | 29.003 | 55.232 | 57.727 | Inf | 269.38 |
| 39 | 14.546 | 14.227 | 30.42 | 27.801 | 59.506 | 61.142 | 270.9 | 281.31 |
| 40 | 15.091 | 15.775 | 27.915 | 28.759 | 57.502 | 46.809 | 256.59 | 254.44 |
| 41 | 13.148 | 21.738 | 25.291 | 33.532 | 65.151 | 49.582 | 301.65 | 251.94 |
| 42 | 15.152 | 15.267 | 29.549 | 27.189 | 58.781 | 57.221 | Inf | Inf |
| 43 | 12.495 | 14.222 | 29.525 | 30.967 | 50.791 | 61.361 | Inf | Inf |
| 44 | 13.608 | 14.021 | 27.7 | 29.729 | 56.018 | 59.324 | Inf | Inf |
| 45 | 15.113 | 15.598 | 26.734 | 29.258 | 55.469 | 56.838 | 284.32 | Inf |
| 46 | 15.855 | 15.561 | 27.344 | 27.487 | 51.35 | 53.21 | 271.15 | 279.09 |
| 47 | 14.843 | 15.669 | 28.196 | 29.255 | 57.016 | 56.563 | Inf | Inf |
| 48 | 14.899 | 14.908 | 29.835 | 28.999 | 53.696 | 60.256 | Inf | Inf |
| 49 | 14.811 | 14.111 | 27.747 | 26.504 | 57.092 | 53.148 | 264.81 | 278.99 |
| 50 | 14.147 | 16.173 | 28.863 | 29.533 | 57.028 | 58.192 | 277.14 | 267.94 |
| 51 | 14.938 | 15.368 | 28.612 | 28.937 | 58.228 | 55.5 | Inf | 274.82 |
| 52 | 16.001 | 14.453 | 27.072 | 27.207 | 57.724 | 57.67 | Inf | Inf |
| 53 | 19.037 | 11.095 | 31.796 | 32.642 | 47.693 | 71.819 | 300.13 | 228.89 |
| 54 | 17.05 | 14.457 | 30.427 | 28.56 | 53.744 | 61.836 | Inf | Inf |
| 55 | 12.256 | 14.909 | 26.809 | 24.92 | 52.461 | 49.294 | 290.02 | 311.59 |
| 56 | 16.325 | 14.763 | 26.088 | 27.069 | 52.5 | 56.791 | 298.24 | Inf |
| 57 | 17.102 | 16.33 | 33.43 | 28.348 | 62.142 | 53.741 | Inf | Inf |
| 58 | 16.477 | 14.299 | 27.903 | 25.256 | 49.492 | 54.879 | Inf | 294.02 |
| 59 | 15.716 | 17.071 | 28.234 | 29.441 | 52.727 | 59.839 | 284.74 | 279.24 |
| 60 | 14.521 | 15.364 | 29.87 | 30.657 | 61.904 | 59.515 | Inf | Inf |
| 61 | 14.304 | 17.143 | 26.97 | 31.799 | 55.888 | 60.799 | Inf | Inf |
| 62 | 16.941 | 16.164 | 29.141 | 33.96 | 55.575 | 56.431 | Inf | 285.21 |
| 63 | 15.042 | 15.421 | 24.862 | 30.471 | 48.008 | 54.162 | 278.47 | Inf |
| 64 | 16.776 | 14.112 | 24.935 | 26.753 | 53.299 | 64.475 | Inf | Inf |
| 65 | 15.554 | 15.305 | 27.797 | 29.078 | 57.719 | 62.719 | Inf | Inf |
| 66 | 17.868 | 13.64 | 33.006 | 29.076 | 66.693 | 59.174 | Inf | Inf |

APPENDIX C

Clinical Trail Subject Data

R104:

| Case No. | Index | Lyapunov Exponents | Estimated Kolmogorov Entropy | Estimated Kaplan-Yorke Dimension | Goodness of Erlang Fit (LSE) |
|---|---|---|---|---|---|
| R104 | Baseline | 0.4257192<br>−0.0170116<br>−0.6356794 | 0.4257192 | 2.642946 | Inf |
| | Placebo | 0.4117576<br>−0.02004995<br>−0.6430027 | 0.4117576 | 2.609185 | Inf |

APPENDIX C-continued

Clinical Trail Subject Data

| | | | | | |
|---|---|---|---|---|---|
| Low Dose | 0.4020163<br>−0.0246642<br>−0.6545819 | 0.4020163 | 2.576478 | Inf | |
| Medium Dose | 0.3728832<br>−0.03939239<br>−0.6454437 | 0.3728832 | 2.516684 | Inf | |
| High Dose | 0.3858872<br>−0.0396689<br>−0.6403063 | 0.3858872 | 2.540707 | Inf | |
| Average | | 0.3996527 | 2.5772 | | |
| STD | | 0.0208427 | 0.050843 | | |

| | Lag = 25 | | 50 | | 100 | | 500 | |
|---|---|---|---|---|---|---|---|---|
| Baseline | 15.052 | 14.810 | 30.699 | 27.967 | 56.789 | 67.423 | Inf | Inf |
| Placebo | 15.808 | 14.017 | 31.859 | 30.733 | 58.897 | 60.310 | Inf | Inf |
| Low Dose | 14.513 | 16.289 | 31.113 | 29.346 | 57.369 | 56.251 | Inf | Inf |
| Medium Dose | 16.215 | 18.367 | 64.036 | 59.299 | 64.036 | 59.299 | Inf | Inf |
| High Dose | 16.803 | 16.214 | 34.137 | 31.680 | 56.526 | 59.293 | Inf | Inf |

R105:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R105 | Baseline | 0.4383994<br>−0.0359339<br>−0.6870821 | 0.4383994 | 2.585760 | 2.20E−05 |
| | Placebo | 0.3808797<br>−0.0550283<br>−0.6826629 | 0.3808797 | 2.477324 | Inf |
| | Low Dose | 0.4504898<br>−0.0226678<br>−0.6736853 | 0.4504898 | 2.635047 | 1.73E−05 |
| | Medium Dose | 0.44423<br>−0.022082<br>−0.65952 | 0.44423 | 2.6400 | 1.56E−05 |
| | High Dose | 0.41724<br>−0.031641<br>−0.68679 | 0.41724 | 2.5614 | Inf |
| | Average | | 0.42624778 | 2.5799062 | |
| | STD | | 0.0282759 | 0.0662413 | |

| | Lag = 25 | | 50 | | 100 | | 500 | |
|---|---|---|---|---|---|---|---|---|
| Baseline | 13.854 | 15.075 | 28.530 | 29.149 | 73.504 | 69.372 | Inf | Inf |
| Placebo | 16.673 | 14.378 | 29.228 | 31.386 | 60.029 | 58.656 | Inf | Inf |
| Low Dose | 17.061 | 17.766 | 29.581 | 31.072 | 66.954 | 64.683 | Inf | Inf |
| Medium Dose | 13.824 | 16.628 | 30.737 | 32.338 | 61.782 | 56.897 | Inf | Inf |
| High Dose | 23.381 | 13.109 | 48.778 | 32.229 | 58.119 | 60.108 | 319.168 | 265.123 |

R106:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R106 | Baseline | 0.4064944<br>−0.0329571<br>−0.6683800 | 0.4064944 | 2.558870 | 1.24E−05 |
| | Placebo | 0.4333435<br>−0.0383438<br>−0.6776672 | 0.4333435 | 2.582881 | 7.14E−06 |
| | Low Dose | 0.449674<br>−0.0139489<br>−0.658808 | 0.449674 | 2.661384 | 1.06E−05 |
| | Medium Dose | 0.4433273<br>−0.023964<br>−0.6736245 | 0.4433273 | 2.622548 | 4.10E−06 |
| | High Dose | 0.4571653<br>−0.0173126<br>−0.6812629 | 0.4571653 | 2.645643 | Inf |
| | Average | | 0.4380009 | 2.6142652 | |
| | STD | | 0.0196612 | 0.0427988 | |

APPENDIX C-continued

Clinical Trail Subject Data

| | Lag = 25 | | 50 | | 100 | | 500 | |
|---|---|---|---|---|---|---|---|---|
| Baseline | 13.980 | 14.477 | 26.900 | 26.726 | 53.245 | 56.105 | Inf | Inf |
| Placebo | 16.019 | 16.136 | 28.791 | 27.599 | 64.869 | 64.492 | Inf | Inf |
| Low Dose | 16.043 | 13.888 | 33.348 | 30.029 | 61.330 | 58.183 | Inf | Inf |
| Medium Dose | 15.224 | 15.989 | 31.130 | 30.764 | 57.209 | 61.457 | Inf | Inf |
| High Dose | 14.639 | 15.773 | 33.686 | 30.595 | 69.401 | 68.378 | Inf | Inf |

R107:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R107 | Baseline | 0.3205683<br>−0.0992338<br>−0.6921756 | 0.3205683 | 2.319766 | 1.85E−05 |
| | Placebo | 0.3066369<br>−0.09702648<br>−0.6948343 | 0.3066369 | 2.301670 | NaN |
| | Low Dose | 0.3368838<br>−0.0839962<br>−0.6913801 | 0.3368838 | 2.365772 | 6.21E−06 |
| | Medium Dose | 0.318106<br>−0.101117<br>−0.709736 | 0.318106 | 2.305732 | 1.38E−06 |
| | High Dose | 0.3489985<br>−0.077165<br>−0.6861377 | 0.3489985 | 2.396179 | 6.98E−06 |
| | Average | | 0.3262387 | 2.3378238 | |
| | STD | | 0.0166872 | 0.0413808 | |

| | Lag = 25 | | 50 | | 100 | | 500 | |
|---|---|---|---|---|---|---|---|---|
| Baseline | 15.427 | 17.456 | 31.820 | 29.071 | 65.263 | 62.130 | Inf | Inf |
| Placebo | 16.035 | 15.031 | 28.974 | 25.695 | 60.983 | 65.712 | Inf | Inf |
| Low Dose | 15.848 | 16.783 | 31.524 | 27.809 | 60.704 | 41.956 | 298.597 | Inf |
| Medium Dose | 14.132 | 14.188 | 28.407 | 31.088 | 57.907 | 61.577 | Inf | Inf |
| High Dose | 13.523 | 21.860 | 21.920 | 29.631 | 82.596 | 46.164 | 269.247 | 361.590 |

R108:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R108 | Baseline | 0.3776069<br>−0.0789358<br>−0.7294197 | 0.3776069 | 2.409464 | 1.62E−05 |
| | Placebo | 0.3218944<br>−0.1189825<br>−0.7438030 | 0.3218944 | 2.272803 | 3.90E−06 |
| | Low Dose | 0.3743164<br>−0.07587542<br>−0.7020173 | 0.3743164 | 2.425119 | 7.09E−06 |
| | Medium Dose | 0.4127410<br>−0.0566170<br>−0.7012472 | 0.4127410 | 2.507844 | 1.54E−05 |
| | High Dose | 0.4332701<br>−0.0324193<br>−0.6791455 | 0.4332701 | 2.590228 | 1.16E−05 |
| | Average | | 0.38396576 | 2.4410916 | |
| | STD | | 0.04255976 | 0.1186107 | |

| | Lag = 25 | | 50 | | 100 | | 500 | |
|---|---|---|---|---|---|---|---|---|
| Baseline | 15.234 | 13.798 | 71.057 | 78.088 | 71.057 | 78.088 | 233.488 | 241.924 |
| Placebo | 25.385 | 24.492 | 37.375 | 36.088 | 60.458 | 60.483 | Inf | 215.364 |
| Low Dose | 17.119 | 16.955 | 28.385 | 31.744 | 91.713 | Inf | 243.071 | Inf |
| Medium Dose | 14.508 | 16.720 | 30.891 | 32.514 | 58.030 | 59.426 | Inf | Inf |
| High Dose | 15.543 | 15.673 | 31.098 | 31.343 | 56.614 | 57.213 | Inf | Inf |

APPENDIX C-continued

Clinical Trail Subject Data

R201:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R201 | Baseline | 0.2284109<br>−0.1270624<br>−0.7144813 | 0.2284109 | 2.141849 | 1.58E−05 |
|  | Placebo | 0.3951689<br>−0.0347777<br>−0.6808515 | 0.3951689 | 2.529324 | 1.64E−05 |
|  | Low Dose | 0.4579045<br>−0.0079399<br>−0.6606626 | 0.4579045 | 2.681081 | 6.01E−06 |
|  | Medium Dose | 0.3941604<br>−0.0430239<br>−0.6620226 | 0.3941604 | 2.530400 | 1.74E−05 |
|  | High Dose | 0.3985903<br>−0.0332158<br>−0.6788887 | 0.3985903 | 2.538195 | 2.71E−05 |
|  | Average |  | 0.374847 | 2.4841698 |  |
|  | STD |  | 0.086156 | 0.2018987 |  |

| | Lag = 25 | | 50 | | 100 | | 500 | |
|---|---|---|---|---|---|---|---|---|
| Baseline | 13.077 | 14.279 | 19.856 | 24.002 | 71.264 | 68.311 | 156.200 | 149.486 |
| Placebo | 17.379 | 16.375 | 30.394 | 30.148 | 62.555 | 64.297 | Inf | Inf |
| Low Dose | 16.427 | 13.964 | 28.665 | 31.015 | 64.732 | 60.448 | Inf | Inf |
| Medium Dose | 15.372 | 16.555 | 57.589 | 61.522 | 57.589 | 61.522 | Inf | Inf |
| High Dose | 17.066 | 16.858 | 28.900 | 31.493 | 57.652 | 59.239 | Inf | Inf |

R202:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R202 | Baseline | 0.4248038<br>−0.01747596<br>−0.6580406 | 0.4248038 | 2.619001 | 2.03E−05 |
|  | Placebo | 0.4291282<br>−0.02000201<br>−0.6633723 | 0.4291282 | 2.616737 | 3.38E−06 |
|  | Low Dose | 0.4239012<br>−0.0201440<br>−0.6744179 | 0.4239012 | 2.598675 | 5.11E−06 |
|  | Medium Dose | 0.4100861<br>−0.0234355<br>−0.6571032 | 0.4100861 | 2.588417 | 3.50E−06 |
|  | High Dose | 0.4102783<br>−0.02448697<br>−0.6585543 | 0.4102783 | 2.585815 | 3.73E−06 |
|  | Average |  | 0.4196395 | 2.601729 |  |
|  | STD |  | 0.0088567 | 0.015519 |  |

| | Lag = 25 | | 50 | | 100 | | 500 | |
|---|---|---|---|---|---|---|---|---|
| Baseline | 16.099 | 15.315 | 28.010 | 28.789 | 58.636 | 57.767 | Inf | Inf |
| Placebo | 16.261 | 15.468 | 29.944 | 33.227 | 66.219 | 62.698 | Inf | Inf |
| Low Dose | 18.026 | 15.744 | 32.099 | 32.397 | 62.654 | 64.756 | Inf | Inf |
| Medium Dose | 15.551 | 15.454 | 30.444 | 30.176 | 68.613 | 60.013 | Inf | Inf |
| High Dose | 15.568 | 16.903 | 29.208 | 32.349 | 62.404 | 61.188 | Inf | Inf |

R203:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R203 | Baseline | 0.3881749<br>−0.0635190<br>−0.6913329 | 0.3881749 | 2.469609 | 1.12E−06 |

APPENDIX C-continued

Clinical Trail Subject Data

|  |  |  |  |  |  |
|---|---|---|---|---|---|
|  | Placebo | 0.4147708 | 0.4147708 | 2.521725 | 4.73E−06 |
|  |  | −0.0491116 |  |  |  |
|  |  | −0.7008653 |  |  |  |
|  | Low Dose | 0.4244452 | 0.4244452 | 2.560483 | 2.65E−06 |
|  |  | −0.0362641 |  |  |  |
|  |  | −0.6925834 |  |  |  |
|  | Medium Dose | 0.3980816 | 0.3980816 | 2.504774 | 1.23E−06 |
|  |  | −0.04892012 |  |  |  |
|  |  | −0.6917190 |  |  |  |
|  | High Dose | 0.4028135 | 0.4028135 | 2.510517 | 1.89E−05 |
|  |  | −0.0502408 |  |  |  |
|  |  | −0.6906193 |  |  |  |
| Average | 0.4056572 | 2.5134216 |  |  |  |
| STD | 0.0142052 | 0.0327356 |  |  |  |

|  | Lag = 25 | 50 | 100 | 500 |  |  |
|---|---|---|---|---|---|---|
| Baseline | 15.266 | 15.222 | 28.638 | 31.876 | Inf | Inf |
| Placebo | 15.598 | 15.824 | 29.816 | 33.919 | Inf | Inf |
| Low Dose | 14.420 | 14.696 | 60.012 | 60.110 | Inf | Inf |
| Medium Dose | 14.126 | 16.378 | 29.839 | 32.319 | Inf | Inf |
| High Dose | 14.303 | 14.935 | 30.472 | 29.939 | Inf | Inf |

R204:

| Case No. | Index (Patient No.) | Lyapunov Exponents | Estimated Kolmogorov Entropy | Estimated Kaplan-Yorke Dimension | Goodness of Erlang Fit (LSE) |
|---|---|---|---|---|---|
| R204 | Baseline | 0.4412964 | 0.4412964 | 2.607837 | 5.18E−06 |
|  |  | −0.02450989 |  |  |  |
|  |  | −0.6856878 |  |  |  |
|  | Placebo | 0.4244762 | 0.4244762 | 2.575992 | 1.49E−06 |
|  |  | −0.03239431 |  |  |  |
|  |  | −0.6807070 |  |  |  |
|  | Low Dose | 0.4278505 | 0.4278505 | 2.535785 | 4.62E−06 |
|  |  | −0.0502191 |  |  |  |
|  |  | −0.7048186 |  |  |  |
|  | Medium Dose | 0.4284803 | 0.4284803 | 2.595601 | 7.80E−06 |
|  |  | −0.0252411 |  |  |  |
|  |  | −0.6770293 |  |  |  |
|  | High Dose | 0.4069436 | 0.4069436 | 2.507459 | 1.16E−05 |
|  |  | −0.0521102 |  |  |  |
|  |  | −0.6.992356 |  |  |  |
|  | Average |  | 0.4258094 | 2.5645348 |  |
|  | STD |  | 0.0123374 | 0.04199897 |  |

|  | Lag = 25 | 50 | 100 |  | 500 |  |  |  |
|---|---|---|---|---|---|---|---|---|
| Baseline | 14.348 | 15.404 | 28.778 | 29.519 | 55.589 | 60.832 | Inf | Inf |
| Placebo | 16.411 | 15.492 | 32.058 | 29.449 | 66.022 | 60.961 | Inf | Inf |
| Low Dose | 15.709 | 15.536 | 32.447 | 30.625 | 54.379 | 62.877 | Inf | Inf |
| Medium Dose | 14.747 | 14.818 | 29.562 | 30.434 | 57.064 | 62.936 | Inf | Inf |
| High Dose | 15.893 | 15.207 | 28.111 | 31.188 | 63.109 | 54.819 | Inf | Inf |

R205:

| Case No. | Index (Patient No.) | Lyapunov Exponents | Estimated Kolmogorov Entropy | Estimated Kaplan-Yorke Dimension | Goodness of Erlang Fit (LSE) | RR-QT or QT-RR |
|---|---|---|---|---|---|---|
| R205 | Baseline | 0.4122025 | 0.4122025 | 2.563903 | 1.40E−05 | QT-RR |
|  |  | −0.0352633 |  |  |  |  |
|  |  | −0.6684468 |  |  |  |  |
|  | Placebo | 0.4339110 | 0.4339110 | 2.627903 | 3.35E−05 | RR-QT |
|  |  | −0.01929673 |  |  |  |  |
|  |  | −0.6603159 |  |  |  |  |
|  | Low Dose | 0.4715819 | 0.474600 | 2.744306 | 2.71E−05 | RR-QT |
|  |  | 0.00301865 |  |  |  |  |
|  |  | −0.6376417 |  |  |  |  |

APPENDIX C-continued

Clinical Trail Subject Data

|  |  |  |  |  |  |
|---|---|---|---|---|---|
| Medium Dose | 0.4397894 −0.0145817 −0.6612745 | 0.4397894 | 2.643012 | 2.86E−05 | QT-RR |
| Average | | 0.4401257 | 2.644781 | | |
| STD | | 0.0258645 | 0.074687 | | |

| | Lag = 25 | | 50 | | 100 | | 500 | |
|---|---|---|---|---|---|---|---|---|
| Baseline | 17.187 | 13.657 | Inf | Inf | Inf | Inf | Inf | Inf |
| Placebo | 14.773 | 15.574 | Inf | Inf | Inf | Inf | Inf | Inf |
| Low Dose | 13.778 | 14.225 | 27.288 | 29.050 | 58.494 | 61.879 | Inf | Inf |
| Medium Dose | 14.452 | 13.857 | 30.453 | 32.576 | 58.996 | 70.487 | Inf | Inf |

R207:

| Case No. | Index (Patient No.) | Lyapunov Exponents | Estimated Kolmogorov Entropy | Estimated Kaplan-Yorke Dimension | Goodness of Erlang Fit (LSE) | RR-QT or QT-RR |
|---|---|---|---|---|---|---|
| R207 | Baseline | 0.3736964 −0.06247597 −0.692537 | 0.3736964 | 2.449392 | 6.11E−06 | QT-RR |
| | Placebo | 0.4432160 −0.0210113 −0.6646048 | 0.4432160 | 2.635272 | 7.17E−06 | QT-RR |
| | Low Dose | 0.3709137 −0.0790944 −0.6992408 | 0.3709137 | 2.417337 | 5.83E−06 | QT-RR |
| | Medium Dose | 0.2479515 −0.1497657 −0.7510070 | 0.2479515 | 2.130739 | NaN | QT-RR |
| | High Dose | 0.4392516 −0.02.93135 −0.6.661058 | 0.4392516 | 2.615425 | 2.39E−05 | RR-QT |
| | Average | | 0.3750058 | 2.449633 | | |
| | STD | | 0.0789642 | 0.202907 | | |

| | Lag = 25 | | 50 | | 100 | | 500 | |
|---|---|---|---|---|---|---|---|---|
| Baseline | 13.888 | 14.226 | 26.668 | 28.524 | 58.862 | 59.220 | Inf | Inf |
| Placebo | 14.608 | 15.955 | 29.947 | 30.609 | 66.690 | 59.010 | Inf | Inf |
| Low Dose | 13.594 | 14.203 | 27.581 | 27.773 | 53.302 | 52.973 | Inf | Inf |
| Medium Dose | 37.236 | 39.076 | 39.019 | 41.077 | 39.019 | 41.077 | 132.386 | 130.343 |
| High Dose | 13.823 | 14.479 | 30.999 | 31.879 | 59.453 | 56.495 | Inf | Inf |

R208:

| Case No. | Index (Patient No.) | Lyapunov Exponents | Estimated Kolmogorov Entropy | Estimated Kaplan-Yorke Dimension | Goodness of Erlang Fit (LSE) | RR-QT or QT-RR |
|---|---|---|---|---|---|---|
| R208 | Baseline | 0.2955212 −0.09143779 −0.6720979 | 0.2955212 | 2.303651 | 3.16E−05 | QT-RR |
| | Placebo | 0.4108713 −0.0307061 −0.6543966 | 0.4108713 | 2.580940 | Inf | QT-RR |
| | Low Dose | 0.4094391 −0.019539 −0.6590926 | 0.4094391 | 2.591571 | 1.41E−05 | QT-RR |
| | Medium Dose | 0.4555751 −0.0117224 −0.6577136 | 0.4555751 | 2.674842 | Inf | RR-QT |
| | High Dose | 0.4461778 −0.0153413 −0.6535721 | 0.4461778 | 2.659203 | Inf | RR-QT |
| | Average | | 0.4035169 | 2.5620414 | | |
| | STD | | 0.0638009 | 0.1501325 | | |

APPENDIX C-continued

| Clinical Trail Subject Data | | | | | | | | |
|---|---|---|---|---|---|---|---|---|
| | Lag = 25 | | 50 | | 100 | | 500 | |
| Baseline | 17.544 | 15.788 | 34.829 | 30.903 | 58.684 | 71.490 | Inf | Inf |
| Placebo | 14.415 | 15.830 | 31.508 | 30.604 | 66.267 | 67.670 | Inf | Inf |
| Low Dose | 16.504 | 14.502 | 32.871 | 28.643 | 57.326 | 55.636 | Inf | Inf |
| Medium Dose | 16.087 | 17.558 | 32.280 | 35.208 | 64.244 | 70.436 | Inf | Inf |

The invention claimed is:

1. A computer-implemented method for diagnosing a risk of cardiac dysfunction associated with a subject, the method executed by one or more computer systems and comprising:
receiving electrocardiogram data associated with a subject, the electrocardiogram data comprising a series of RR intervals and a series of QT intervals, wherein the series RR intervals corresponds, in part, to the series of QT intervals;
generating a first value which indicates an amount by which uncertainty associated with the series of QT intervals is reduced given the series of RR intervals;
generating a second value which indicates an amount by which uncertainty associated with the series of RR intervals is reduced given the series of QT intervals;
determining the subject to be associated with a low risk of cardiac dysfunction responsive to the first value exceeding the second value; and
providing a result of the determination.

2. The method of claim 1, wherein determining the subject to be associated with the low risk of cardiac dysfunction further comprises:
determining that a histogram generated based on the series of RR intervals fits an Erlang distribution.

3. The method of claim 2, wherein determining that the histogram generated based on the series of RR intervals fits an Erlang distribution comprises:
generating a coefficient, wherein the coefficient describes a fit between the series of RR intervals and an Erlang distribution; and
determining that the coefficient does not exceed a threshold value.

4. The method of claim 1, wherein the first value and the second value represent Komolgorov-Sinai mutual information values and are generated using a lag of 500.

5. The method of claim 1, further comprising:
determining that the subject is associated with a high risk of cardiac dysfunction responsive to the second value exceeding the first value.

6. The method of claim 5, wherein determining that the subject is associated with the high risk of cardiac dysfunction further comprises:
determining that a histogram generated based on the series of RR intervals does not fit an Erlang Distribution.

7. The method of claim 5, further comprising:
determining whether the high risk of cardiac dysfunction is due to intrinsic dysfunction or extrinsic dysfunction.

8. The method of claim 7, wherein determining whether the high risk of cardiac dysfunction is due to intrinsic dysfunction or extrinsic dysfunction comprises:
determining whether a stationarity value exceeds a threshold value;
determine that the high risk of cardiac dysfunction is due to intrinsic dysfunction responsive to the stationarity metric exceeding the threshold value; and
determine that the high risk of cardiac dysfunction is due to extrinsic function responsive to the stationarity metric not exceeding the threshold value.

9. The method of claim 5, wherein electrocardiogram data is derived from a subject who has been treated with a compound.

10. The method of claim 1, wherein determining that the subject is associated with the low risk of cardiac dysfunction further comprises:
determining one or more Lyapunov coefficients based on the series of RR intervals; and
determining that the subject is associated with a low risk of cardiac dysfunction responsive to the one or more Lyapunov coefficients exceeding a value of zero.

11. A computer system for diagnosing a risk of cardiac dysfunction associated with a subject, the system comprises one or more computer systems and a memory, the system further comprising:
a reporting module stored in the memory and adapted to receive electrocardiogram data associated with a subject, the electrocardiogram data comprising a series of RR intervals and a series of QT intervals, wherein the series RR intervals corresponds, in part, to the series of QT intervals;
a mutual information module stored in the memory and adapted to generate a first value which indicates an amount by which uncertainty associated with the series of QT intervals is reduced given the series of RR intervals and a second value which indicates an amount by which uncertainty associated with the series of RR intervals is reduced given the series of QT intervals;
a diagnosis module stored in the memory and adapted to determine the subject to be associated with a low risk of cardiac dysfunction responsive to the first value exceeding the second value; and
a visualization module stored in the memory and adapted to provide a result of the determination.

12. The system of claim 11, further comprising an Erlang fitting module stored in the memory and adapted to:
determine that a histogram generated based on the series of RR intervals fits an Erlang distribution.

13. The system of claim 12, wherein the diagnosis module is further adapted to:
generate a coefficient, wherein the coefficient describes a fit between the histogram generated based on the series of RR intervals and an Erlang distribution; and
determine that the subject is associated with a low risk of cardiac dysfunction responsive to the coefficient below a threshold value.

14. The system of claim 13, wherein the first value and the second value represent Komolgorov-Sinai mutual information values and the mutual information module is further adapted to generate the first value and the second value based on a lag of 500.

15. The system of claim 14, wherein the diagnosis module is further adapted to:
  determine that the subject is associated with a high risk of cardiac dysfunction responsive to determining that the series of RR intervals do not fit an Erlang Distribution.

16. The system of claim 11, wherein the diagnosis module is further adapted to:
  determine that the subject is associated with a high risk of cardiac dysfunction responsive to the second value exceeding the first value.

17. The system of claim 16, wherein the diagnosis module is further adapted to:
  determine whether the high risk of cardiac dysfunction is due to intrinsic dysfunction or extrinsic dysfunction.

18. The system of claim 17, wherein the diagnosis module is further adapted to:
  determine whether a stationarity value exceeds a threshold value;
  determine that the high risk of cardiac dysfunction is due to intrinsic cardiac dysfunction responsive to the stationarity metric exceeding the threshold value; and
  determine that the high risk of cardiac dysfunction is due to extrinsic cardiac dysfunction responsive to the stationarity metric not exceeding the threshold value.

19. A computer-readable storage medium encoded with executable computer program code for diagnosing a risk of cardiac dysfunction associated with a subject, the program code comprising program code for:
  receiving electrocardiogram data associated with a subject, the electrocardiogram data comprising a series of RR intervals and a series of QT intervals, wherein the series RR intervals corresponds, in part, to the series of QT intervals;
  generating a first value which indicates an amount by which uncertainty associated with the QT intervals is reduced given the RR intervals;
  generating a second value which indicates an amount by which uncertainty associated with the RR intervals is reduced given the QT intervals; and
  determining the subject to be associated with a low risk of cardiac dysfunction responsive to the first value exceeding the second value; and
  providing a result of the determination.

20. The medium of claim 19, wherein program code for determining the subject to be associated with a low risk of cardiac dysfunction comprises program code for:
  determining that a histogram generated based on the series of RR intervals fits an Erlang distribution.

21. The medium of claim 20, wherein program code for determining that the histogram generated based on the series of RR intervals fits an Erlang distribution comprises program code for:
  generating a coefficient, wherein the coefficient describes a fit between the series of RR intervals and an Erlang distribution; and
  determining that the coefficient does not exceed a threshold value.

22. The medium of claim 19, further comprising program code for:
  determining that the subject is associated with a high risk of cardiac dysfunction responsive to the second value exceeding the first value.

23. The medium of claim 22, wherein the diagnosis module is further adapted to:
  determine whether the high risk of cardiac dysfunction is due to intrinsic dysfunction or extrinsic dysfunction.

24. The medium of claim 23, wherein the diagnosis module is further adapted to:
  determine whether a stationarity value exceeds a threshold value;
  determine that the high risk of cardiac dysfunction is due to intrinsic cardiac dysfunction responsive to the stationarity value exceeding the threshold value; and
  determine that the high risk of cardiac dysfunction is due to extrinsic function responsive to the stationarity value not exceeding the threshold value.

25. The medium of claim 22, wherein program code for determining that the subject is associated with a high risk of cardiac dysfunction further comprises program code for:
  determining that a histogram generated based on the series of RR intervals does not fit an Erlang Distribution.

* * * * *